United States Patent
Pulé et al.

(10) Patent No.: US 10,745,715 B2
(45) Date of Patent: Aug. 18, 2020

(54) METHOD AND MEANS FOR PURIFYING RETROVIRAL VECTORS

(71) Applicant: UCL BUSINESS PLC, London (GB)

(72) Inventors: Martin Pulé, London (GB); Leila Mekkaoui, London (GB); Gordon Weng-Kit Cheung, London (GB)

(73) Assignee: UCL BUSINESS LTD, London (GB)

( * ) Notice: Subject to any disclaimer, the term of this patent is extended or adjusted under 35 U.S.C. 154(b) by 0 days.

(21) Appl. No.: 15/506,391

(22) PCT Filed: Aug. 28, 2015

(86) PCT No.: PCT/GB2015/052493
§ 371 (c)(1),
(2) Date: Feb. 24, 2017

(87) PCT Pub. No.: WO2016/030690
PCT Pub. Date: Mar. 3, 2016

(65) Prior Publication Data
US 2017/0240920 A1    Aug. 24, 2017

(30) Foreign Application Priority Data
Aug. 29, 2014 (GB) .................................. 1415344.9

(51) Int. Cl.
| | | |
|---|---|---|
| *C12Q 1/68* | (2018.01) | |
| *C12Q 1/6811* | (2018.01) | |
| *C12Q 1/70* | (2006.01) | |
| *C12N 15/86* | (2006.01) | |
| *C07K 14/705* | (2006.01) | |
| *C12N 15/64* | (2006.01) | |

(52) U.S. Cl.
CPC ........ *C12N 15/86* (2013.01); *C07K 14/70517* (2013.01); *C12N 15/64* (2013.01); *C07K 2319/03* (2013.01); *C07K 2319/21* (2013.01); *C07K 2319/22* (2013.01); *C07K 2319/23* (2013.01); *C07K 2319/50* (2013.01); *C12N 2740/10041* (2013.01); *C12N 2740/10051* (2013.01); *C12N 2740/10052* (2013.01); *C12N 2740/15043* (2013.01); *C12N 2740/15051* (2013.01)

(58) Field of Classification Search
None
See application file for complete search history.

(56) References Cited

U.S. PATENT DOCUMENTS

| | | | | |
|---|---|---|---|---|
| 2006/0292682 | A1* | 12/2006 | Hawkins | C12N 15/86 435/235.1 |
| 2015/0023933 | A1* | 1/2015 | Collins | C12N 7/00 424/93.21 |
| 2017/0267756 | A1* | 9/2017 | Riddell | C07K 16/2803 |
| 2018/0066280 | A1 | 3/2018 | Pule et al. | |

FOREIGN PATENT DOCUMENTS

| | | | |
|---|---|---|---|
| CN | 103267841 | * | 8/2013 |
| CN | 103267841 A | * | 8/2013 |
| WO | WO-92/05266 A2 | | 4/1992 |
| WO | WO-94/29438 A1 | | 12/1994 |
| WO | WO-97/27310 A1 | | 7/1997 |
| WO | WO-2004/000220 A2 | | 12/2003 |
| WO | WO-2007/095201 A2 | | 8/2007 |
| WO | WO-2011/067553 A1 | | 6/2011 |
| WO | WO-2013/153391 A1 | | 10/2013 |
| WO | WO-2014/121005 A1 | | 8/2014 |
| WO | WO-2015/095895 A1 | | 6/2015 |
| WO | WO-2018/033726 A1 | | 2/2018 |

OTHER PUBLICATIONS

Korndörfer et al., Improved affinity of engineered streptavidin for the Strep-tag II peptide is due to a fixed open conformation of the lid-like loop at the binding site Protein Science (2002), 11:883-893.*
Giebel et al Screening of cyclic peptide phage libraries identifies ligands that bind streptavidin with high affinities Biochemistry. Nov. 28, 1995;34(47):15430-5.*
Chivers et al. A streptavidin variant with slower biotin dissociation and increased mechanostability Nat Methods. May 2010 ; 7(5): 391-393.*
Katz, Binding to protein targets of peptidic leads discovered by phage display: crystal structures of streptavidin-bound linear and cyclic peptide ligands containing the HPQ sequence, Biochemistry, 34(47):15421-9 (1995).
Ikeda et al., Continuous high-titer HIV-1 vector production, Nat. Biotechnol., 21(5):569-72 (2003).
International Search Report and Written Opinion, International Application No. pCT/GB2015/052493, dated Oct. 16, 2015.
Katane et al., Factors affecting the direct targeting of murine leukemia virus vectors containing peptide ligands in the envelope protein, EMBO Rep., 3(9):899-904 (2002).
Keefe et al., One-step purification of recombinant proteins using a nanomolar-affinity streptavidin-binding peptide, the SBP-Tag, Protein Expr. Purif., 2393):440-6 (2001).

(Continued)

*Primary Examiner* — Maria G Leavitt
(74) *Attorney, Agent, or Firm* — Marshall, Gerstein & Borun LLP

(57) ABSTRACT

The present invention relates to a producer cell which expresses a tagging protein at the cell surface, such that retroviral vectors produced by the cell are tagged with the tagging protein, wherein the tagging protein comprises: i) a binding domain which binds to a capture moiety ii) a spacer; and iii) a membrane targeting domain such that, when incorporated a retroviral vector, the tagging protein facilitates purification of the retroviral vector from cellular supernatant via binding of the tagging protein to the capture moiety. The present invention also relates to a retroviral vector comprising such a producer cell-derived tagging protein.

20 Claims, 19 Drawing Sheets

Specification includes a Sequence Listing.

(56) References Cited

OTHER PUBLICATIONS

Kinoshita et al., GPI-anchor synthesis in mammalian cells: genes, their products, and a deficiency, J. Biochem., 122(2):251-7 (1997).

Lamla et al., The Nano-tag, a streptavidin-binding peptide for the purification and detection of recombinant proteins, Protein Expr. Purif., 33(1):39-47 (2004).

Lewis et al., Human immunodeficiency virus infection of cells arrested in the cell cycle, EMBO J., 11(8):3053-8 (1992).

Li et al., Mimotope vaccination for epitope-specific induction of anti-CD20 antibodies, Cell Immunol., 239(2):136-43 (2006).

Nesbeth et al., Metabolic biotinylation of lentiviral pseudotypes for scalable paramagnetic microparticle-dependent manipulation, Mol. Ther., 13(4):814-22 (2006).

Parrott et al., Metabolically biotinylated adenovirus for cell targeting, ligand screening, and vector purification, Mol. Ther., 8(4):688-700 (2003).

Perosa et al., Identification of an antigenic and immunogenic motif expressed by two 7-mer rituximab-specific cyclic peptide mimotopes: implication for peptide-based active immunotherapy, J. Immunol., 179(11):7967-74 (2007).

Sandrin et al., Lentiviral vectors pseudotyped with a modified RD114 envelope glycoprotein show increased stability in sera and augmented transduction of primary lymphocytes and CD34+ cells derived from human and nonhuman primates, Blood, 100(3):823-32 (2002).

Schmidt et al., Molecular interaction between the Strep-tag affinity peptide and its cognate target, streptavidin, J. Mol. Biol., 255(5):753-66 (1996).

Schmidt et al., The random peptide library-assisted engineering of a C-terminal affinity peptide, useful for the detection and purification of a functional Ig Fv fragment, Protein Eng., 691):109-22 (1993).

Udomsinprasert et al., Identification, characterization and structure of a new Delta class glutathione transferase isoenzyme, Biochem. J., 388(Pt. 3):763-71 (2005).

Verma et al., Gene therapy—promises, problems and prospects, Nature, 389(6648):239-42 (1997).

Williams et al., Affinity capture of a biotinylated retrovirus on macroporous monolithic adsorbents: towards a rapid single-step purification process, Biotechnol. Bioeng., 89(7):783-7 (2005).

Williams et al., Affinity recovery of Moloney Murine Leukaemia Virus, J. Chromatogr. B Analyt. Technol. Biomed. Life Sci., 820(1):111-9 (2005).

Wu et al., Adenovirus targeting to prostate-specific membrane antigen through virus-displayed, semirandom peptide library screening, Cancer Res., 70(23):9549-53 (2010).

Ye et al., Tagging retrovirus vectors with a metal binding peptide and one-step purification by immobilized metal affinity chromatography, J. Virol., 78(18):9820-7 (2004).

Yu et al., Selection of novel vesicular stomatitis virus glycoprotein variants from a peptide insertion library for enhanced purification of retroviral and lentiviral vectors, J. Virol., 80(7):3285-92 (2006).

U.S. Appl. No. 15/554,499 (2018-0066280), filed Aug. 30, 2017.

* cited by examiner

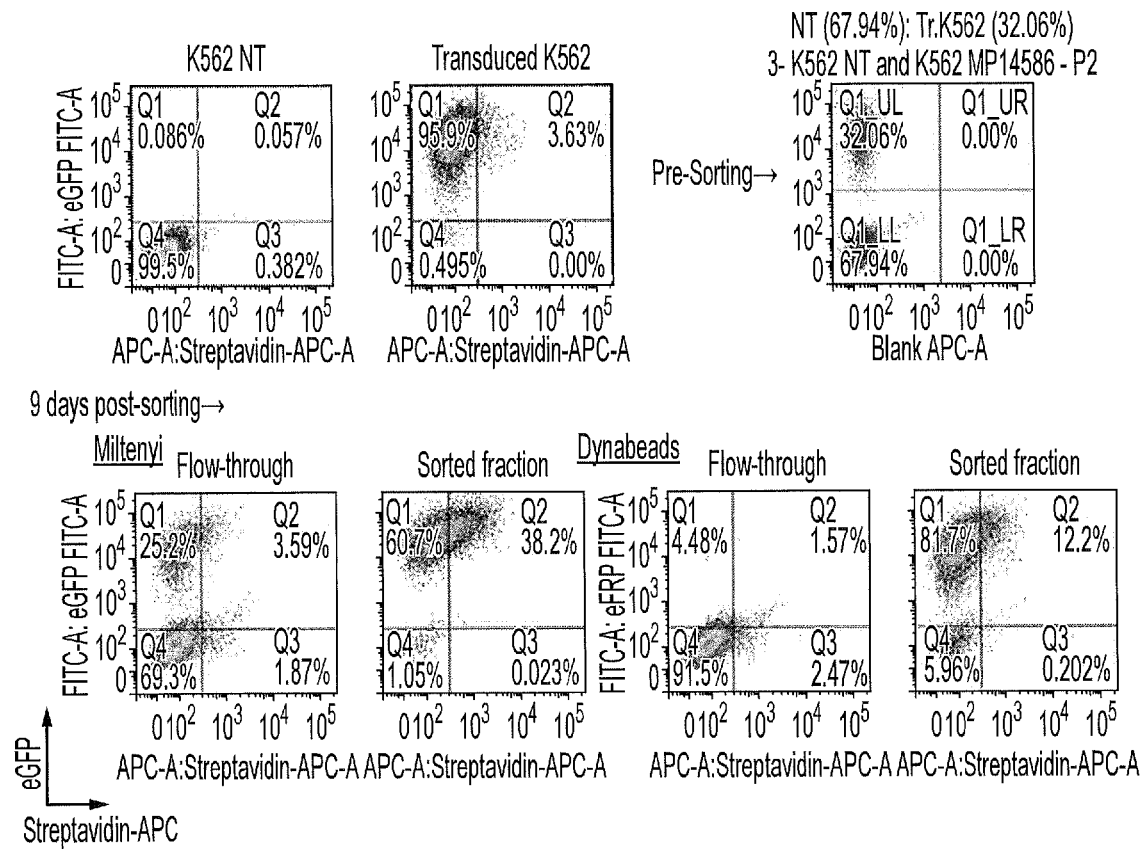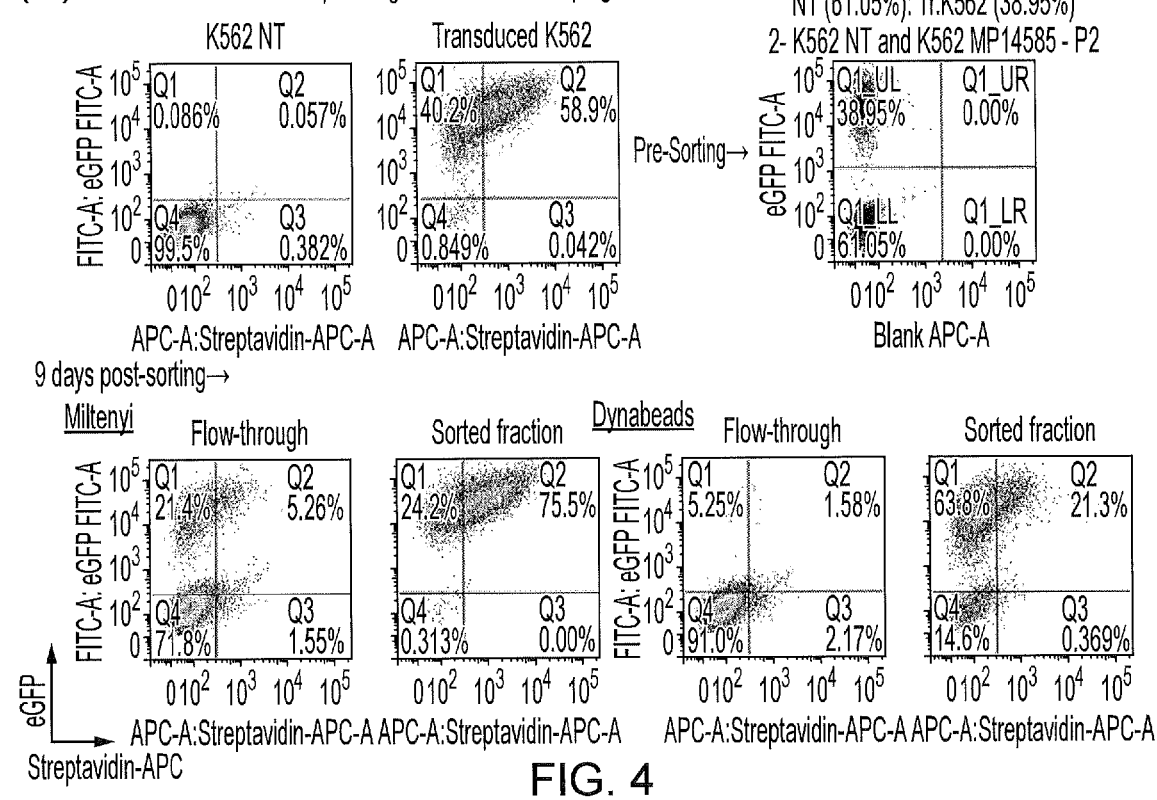
FIG. 4

A) Flankedccstreptag-L8 amino acid sequence:

SEQ ID NO: 47

MGTSLLCWMALCLLGADHADA ECHPQGPPCIEGRKS GGGGS PAPRPPTPAPTIASQP
LSLRPEACRPAAGGAVHTRGLDFACDIYIWAPLAGTCGVLLLSLVITLYCNHRNRRR
VCKCPRPVV

Signal peptide – Flankedccstreptag – Linker – CD8 Stalk

B) Glutathione S-transferases-L8 (GST-L8) amino acid sequence:

SEQ ID NO: 48

MGTSLLCWMALCLLGADHADA MSPILGYWKIKGLVQPTRLLLEYLEEKYEEHLYERD
EGDKWRNKKFELGLEFPNLPYYIDGDVKLTQSMAIIRYIADKHNMLGGCPKERAEIS
MLEGAVLDIRYGVSRIAYSKDFETLKVDFLSKLPEMLKMFEDRLCHKTYLNGDHVTH
PDFMLYDALDVVLYMDPMCLDAFPKLVCFKKRIEAIPQIDKYLKSSKYIAWPLQGWQ
ATFGGGDHPPKSDLEVLFQGPLG SGGGGS PAPRPPTPAPTIASQPLSLRPEACRPAA
GGAVHTRGLDFACDIYIWAPLAGTCGVLLLSLVITLYCNHRNRRRVCKCPRPVV

Signal peptide – GST – Linker – CD8 Stalk

C) RTXep-QBEND10ep-RTXep-L8 (RQR8-L8) amino acid sequence:

SEQ ID NO: 49

MGTSLLCWMALCLLGADHADA CPYSNPSLC SGGGGS ELPTQGTFSNVSTNVSPAKPT
TTA CPYSNPSLC SGGGGS PAPRPPTPAPTIASQPLSLRPEACRPAAGGAVHTRGLDF
ACDIYIWAPLAGTCGVLLLSLVITLYCNHRNRRRVCKCPRPVV

Signal peptide – Rituximab epitope – Linker – Qbend10 – Linker –
Rituximab epitope – Linker – CD8 Stalk D) H6-L-8 amino acid sequence

SEQ ID NO: 50

MGTSLLCWMALCLLGADHADA SHHHHHH SGGGGS PAPRPPTPAPTIASQPLSLRPEA
CRPAAGGAVHTRGLDFACDIYIWAPLAGTCGVLLLSLVITLYCNHRNRRRVCKCPRP
VV

Signal peptide – HexaHis – Linker – CD8 Stalk

FIG. 7

(a) RQR8 tagging of RD114 SU (SEQ ID NO: 31)

MKLPTGMVILCSLIIVRACPYSNPSLCSGGGGSELPTQGTFSNVSTNVSPAKPTTTACPYSNPSLCSG
GGGSGFDDPRKAIALVQKQHGKPCECSGGQVSEAPPNSIQQVTCPGKTAYLMTNQKWKCRVTPKNLTP
SGGELQNCPCNTFQDSMHSSCYTEYRQCRANNKTYYTATLLKIRSGSLNEVQILQNPNQLLQSPCRGS
INQPVCWSATAPIHISDGGGPLDTKRVWTVQKRLEQIHKAMHPELQYHPLALPKVRDDLSLDARTFDI
LNTTFRLLQMSNFSLAQDCWLCLKLGTPTPLAIPTPSLTYSLADSLANASCQIIPPLLVQPMQFSNSS
CLSSPFINDTEQIDLGAVTFTNCTSVANVSSPLCALNGSVFLCGNNMAYTYLPQNWTGLCVQASLLPD
IDIIPGDEPVPIPAIDHYIHRPKRAVQFIPLLAGLGITAAFTTGATGLGVSVTQYTKLSHQLISDVQV
LSGTIQDLQDQVDSLAEVVLQNRRGLDLLTAEQGGICLALQEKCCFYANKSGIVRNKIRTLQEELQKR
RESLASNPLWTGLQGFLP*YLLPLLGPLLTLLLILTIGPCVF*SRLMAFINDRLNVSQNYPIVQQYQALK
AEEEAQD

(b) RQR tagging of RD114 TM (SEQ ID NO: 32)

MKLPTGMVILCSLIIVRAGFDDPRKAIALVQKQHGKPCECSGGQVSEAPPNSIQQVTCPGKTAYLMTN
QKWKCRVTPKNLTPSGGELQNCPCNTFQDSMHSSCYTEYRQCRANNKTYYTATLLKIRSGSLNEVQIL
QNPNQLLQSPCRGSINQPVCWSATAPIHISDGGGPLDTKRVWTVQKRLEQIHKAMHPELQYHPLALPK
VRDDLSLDARTFDILNTTFRLLQMSNFSLAQDCWLCLKLGTPTPLAIPTPSLTYSLADSLANASCQII
PPLLVQPMQFSNSSCLSSPFINDTEQIDLGAVTFTNCTSVANVSSPLCALNGSVFLCGNNMAYTYLPQ
NWTGLCVQASLLPDIDIIPGDEPVPIPAIDHYIHRPKRCPYSNPSLCSGGGGSELPTQGTFSNVS
TNVSPAKPTTTACPYSNPSLCSGGGGSAVQFIPLLAGLGITAAFTTGATGLGVSVTQYTKLSHQL
ISDVQVLSGTIQDLQDQVDSLAEVVLQNRRGLDLLTAEQGGICLALQEKCCFYANKSGIVRNKIRTLQ
EELQKRRESLASNPLWTGLQGFLP*YLLPLLGPLLTLLLILTIGPCVF*SRLMAFINDRLNVSQNYPIVQ
QYQALKAEEEAQD

(c) Flankedcc streptagging of RD114 SU (SEQ ID NO: 33)

MKLPTGMVILCSLIIVRAECHPQGPPCIEGRKSGGGGSGFDDPRKAIALVQKQHGKPCECSGGQVSEA
PPNSIQQVTCPGKTAYLMTNQKWKCRVTPKNLTPSGGELQNCPCNTFQDSMHSSCYTEYRQCRANNKT
YYTATLLKIRSGSLNEVQILQNPNQLLQSPCRGSINQPVCWSATAPIHISDGGGPLDTKRVWTVQKRL
EQIHKAMHPELQYHPLALPKVRDDLSLDARTFDILNTTFRLLQMSNFSLAQDCWLCLKLGTPTPLAIP
TPSLTYSLADSLANASCQIIPPLLVQPMQFSNSSCLSSPFINDTEQIDLGAVTFTNCTSVANVSSPLC
ALNGSVFLCGNNMAYTYLPQNWTGLCVQASLLPDIDIIPGDEPVPIPAIDHYIHRPKRAVQFIPLLAG
LGITAAFTTGATGLGVSVTQYTKLSHQLISDVQVLSGTIQDLQDQVDSLAEVVLQNRRGLDLLTAEQG
GICLALQEKCCFYANKSGIVRNKIRTLQEELQKRRESLASNPLWTGLQGFLP***YLLPLLGPLLTLLLIL
TIGPCVF***SRLMAFINDRLNVSQNYPIVQQYQALKAEEEAQD

(d) flanked cc streptagging of RD114 TM (SEQ ID NO: 34)

MKLPTGMVILCSLIIVRAGFDDPRKAIALVQKQHGKPCECSGGQVSEAPPNSIQQVTCPGKTAYLMTN
QKWKCRVTPKNLTPSGGELQNCPCNTFQDSMHSSCYTEYRQCRANNKTYYTATLLKIRSGSLNEVQIL
QNPNQLLQSPCRGSINQPVCWSATAPIHISDGGGPLDTKRVWTVQKRLEQIHKAMHPELQYHPLALPK
VRDDLSLDARTFDILNTTFRLLQMSNFSLAQDCWLCLKLGTPTPLAIPTPSLTYSLADSLANASCQII
PPLLVQPMQFSNSSCLSSPFINDTEQIDLGAVTFTNCTSVANVSSPLCALNGSVFLCGNNMAYTYLPQ
NWTGLCVQASLLPDIDIIPGDEPVPIPAIDHYIHRPKRECHPQGPPCIEGRKSGGGGSAVQFIPLLAG
LGITAAFTTGATGLGVSVTQYTKLSHQLISDVQVLSGTIQDLQDQVDSLAEVVLQNRRGLDLLTAEQG
GICLALQEKCCFYANKSGIVRNKIRTLQEELQKRRESLASNPLWTGLQGFLP***YLLPLLGPLLTLLLIL
TIGPCVF***SRLMAFINDRLNVSQNYPIVQQYQALKAEEEAQD

FIG. 14 pRDpro amino acid sequence (SEQ ID NO: 39):
MKLPTGMVILCSLIIVRAGFDDPRKAIALVQKQHGKPCECSGGQVSEAPPNSIQQVTCPG
KTAYLMTNQKWKCRVTPKNLTPSGGELQNCPCNTFQDSMHSSCYTEYRQCRANNKTYYTA
TLLKIRSGSLNEVQILQNPNQLLQSPCRGSINQPVCWSATAPIHISDGGGPLDTKRVWTV
QKRLEQIHKAMHPELQYHPLALPKVRDDLSLDARTFDILNTTFRLLQMSNFSLAQDCWLC
LKLGTPTPLAIPTPSLTYSLADSLANASCQIIPPLLVQPMQFSNSSCLSSPFINDTEQID
LGAVTFTNCTSVANVSSPLCALNGSVFLCGNNMAYTYLPQNWTGLCVQASLLPDIDIIPG
DEPVPIPAIDHYIHRPKRAVQFIPLLAGLGITAAFTTGATGLGVSVTQYTKLSHQLISDV
QVLSGTIQDLQDQVDSLAEVVLQNRRGLDLLTAEQGGICLALQEKCCFYANKSGIVRNKI
RTLQEELQKRRESLASNPLWTGLQGFLP**YLLPLLGPLLTLLLILTIGPCVFSRLMAFIND
RLNVSQNYPIVQQYQALKAEEEAQD**

RD114 amino acid sequence (SEQ ID NO: 40):
MKLPTGMVILCSLIIVRAGFDDPRKAIALVQKQHGKPCECSGGQVSEAPPNSIQQVTCPG
KTAYLMTNQKWKCRVTPKISPSGGELQNCPCNTFQDSMHSSCYTEYRQCRRINKTYYTAT
LLKIRSGSLNEVQILQNPNQLLQSPCRGSINQPVCWSATAPIHISDGGGPLDTKRVWTVQ
KRLEQIHKAMTPELQYHPLALPKVRDDLSLDARTFDILNTTFRLLQMSNFSLAQDCWLCL
KLGTPTPLAIPTPSLTYSLADSLANASCQIIPPLLVQPMQFSNSSCLSSPFINDTEQIDL
GAVTFTNCTSVANVSSPLCALNGSVFLCGNNMAYTYLPQNWTRLCVQASLLPDIDINPGD
EPVPIPAIDHYIHRPKRAVQFIPLLAGLGITAAFTTGATGLGVSVTQYTKLSHQLISDVQ
VLSGTIQDLQDQVDSLAEVVLQNRRGLDLLTAEQGGICLALQEKCCFYANKSGIVRNKIR
TLQEELQKRRESLATNPLWTGLQGFLP**YLLPLLGPLLTLLLILTIGPCVFSRLMAFINDR
LNVVHAMVLAQQYQALKAEEEAQD**

FIG. 16

SEQUENCE LISTING

<160> NUMBER OF SEQ ID NOS: 52

<210> SEQ ID NO 1
<211> LENGTH: 8
<212> TYPE: PRT
<213> ORGANISM: Artificial Sequence
<220> FEATURE:
<223> OTHER INFORMATION: Biotin mimicking peptide, streptagII

<400> SEQUENCE: 1

Trp Ser His Pro Gln Phe Glu Lys
1               5

<210> SEQ ID NO 2
<211> LENGTH: 15
<212> TYPE: PRT
<213> ORGANISM: Artificial Sequence
<220> FEATURE:
<223> OTHER INFORMATION: Biotin mimicking peptide, flankedccstreptag

<400> SEQUENCE: 2

Ala Glu Cys His Pro Gln Gly Pro Pro Cys Ile Glu Gly Arg Lys
1               5                   10                  15

<210> SEQ ID NO 3
<211> LENGTH: 8
<212> TYPE: PRT
<213> ORGANISM: Artificial Sequence
<220> FEATURE:
<223> OTHER INFORMATION: Biotin mimicking peptide, ccstreptag

<400> SEQUENCE: 3

Cys His Pro Gln Gly Pro Pro Cys
1               5

<210> SEQ ID NO 4
<211> LENGTH: 36
<212> TYPE: PRT
<213> ORGANISM: Artificial Sequence
<220> FEATURE:
<223> OTHER INFORMATION: Binding domain StreptagII-d8-x2

<400> SEQUENCE: 4

Trp Ser His Pro Gln Phe Glu Lys Ser Gly Gly Gly Gly Ser Pro Ala
1               5                   10                  15

Pro Arg Pro Pro Thr Pro Ala Pro Thr Ile Ala Ser Trp Ser His Pro
            20                  25                  30

Gln Phe Glu Lys
        35

<210> SEQ ID NO 5
<211> LENGTH: 50
<212> TYPE: PRT
<213> ORGANISM: Artificial Sequence
<220> FEATURE:
<223> OTHER INFORMATION: Binding domain Flankedccstreptag-d8-x2

<400> SEQUENCE: 5

Glu Cys His Pro Gln Gly Pro Pro Cys Ile Glu Gly Arg Lys Ser Ser
1               5                   10                  15

Gly Gly Gly Gly Ser Pro Ala Pro Arg Pro Pro Thr Pro Ala Pro Thr
            20                  25                  30

Ile Ala Ser Glu Cys His Pro Gln Gly Pro Pro Cys Ile Glu Gly Arg
        35                  40                  45

-continued

```
Lys Ser
    50

<210> SEQ ID NO 6
<211> LENGTH: 251
<212> TYPE: PRT
<213> ORGANISM: Artificial Sequence
<220> FEATURE:
<223> OTHER INFORMATION: glutathione S-transferase (GST) domain

<400> SEQUENCE: 6

Met Gly Thr Ser Leu Leu Cys Trp Met Ala Leu Cys Leu Leu Gly Ala
1               5                   10                  15

Asp His Ala Asp Ala Met Ser Pro Ile Leu Gly Tyr Trp Lys Ile Lys
            20                  25                  30

Gly Leu Val Gln Pro Thr Arg Leu Leu Leu Glu Tyr Leu Glu Glu Lys
        35                  40                  45

Tyr Glu Glu His Leu Tyr Glu Arg Asp Glu Gly Asp Lys Trp Arg Asn
    50                  55                  60

Lys Lys Phe Glu Leu Gly Leu Glu Phe Pro Asn Leu Pro Tyr Tyr Ile
65                  70                  75                  80

Asp Gly Asp Val Lys Leu Thr Gln Ser Met Ala Ile Ile Arg Tyr Ile
                85                  90                  95

Ala Asp Lys His Asn Met Leu Gly Gly Cys Pro Lys Glu Arg Ala Glu
            100                 105                 110

Ile Ser Met Leu Glu Gly Ala Val Leu Asp Ile Arg Tyr Gly Val Ser
        115                 120                 125

Arg Ile Ala Tyr Ser Lys Asp Phe Glu Thr Leu Lys Val Asp Phe Leu
    130                 135                 140

Ser Lys Leu Pro Glu Met Leu Lys Met Phe Glu Asp Arg Leu Cys His
145                 150                 155                 160

Lys Thr Tyr Leu Asn Gly Asp His Val Thr His Pro Asp Phe Met Leu
                165                 170                 175

Tyr Asp Ala Leu Asp Val Val Leu Tyr Met Asp Pro Met Cys Leu Asp
            180                 185                 190

Ala Phe Pro Lys Leu Val Cys Phe Lys Lys Arg Ile Glu Ala Ile Pro
        195                 200                 205

Gln Ile Asp Lys Tyr Leu Lys Ser Ser Lys Tyr Ile Ala Trp Pro Leu
    210                 215                 220

Gln Gly Trp Gln Ala Thr Phe Gly Gly Gly Asp His Pro Pro Lys Ser
225                 230                 235                 240

Asp Leu Glu Val Leu Phe Gln Gly Pro Leu Gly
                245                 250

<210> SEQ ID NO 7
<211> LENGTH: 17
<212> TYPE: PRT
<213> ORGANISM: Artificial Sequence
<220> FEATURE:
<223> OTHER INFORMATION: Rituximab-binding epitope sequence

<400> SEQUENCE: 7

Cys Glu Pro Ala Asn Pro Ser Glu Lys Asn Ser Pro Ser Thr Gln Tyr
1               5                   10                  15

Cys

<210> SEQ ID NO 8
<211> LENGTH: 10
```

```
<212> TYPE: PRT
<213> ORGANISM: Artificial Sequence
<220> FEATURE:
<223> OTHER INFORMATION: cysteine-constrained 7-mer cyclic peptide R15-C

<400> SEQUENCE: 8

Ala Cys Pro Tyr Ala Asn Pro Ser Leu Cys
1               5                   10

<210> SEQ ID NO 9
<211> LENGTH: 10
<212> TYPE: PRT
<213> ORGANISM: Artificial Sequence
<220> FEATURE:
<223> OTHER INFORMATION: cysteine-constrained 7-mer cyclic peptide R3-C

<400> SEQUENCE: 9

Ala Cys Pro Tyr Ser Asn Pro Ser Leu Cys
1               5                   10

<210> SEQ ID NO 10
<211> LENGTH: 10
<212> TYPE: PRT
<213> ORGANISM: Artificial Sequence
<220> FEATURE:
<223> OTHER INFORMATION: cysteine-constrained 7-mer cyclic peptide R7-C

<400> SEQUENCE: 10

Ala Cys Pro Phe Ala Asn Pro Ser Thr Cys
1               5                   10

<210> SEQ ID NO 11
<211> LENGTH: 10
<212> TYPE: PRT
<213> ORGANISM: Artificial Sequence
<220> FEATURE:
<223> OTHER INFORMATION: cysteine-constrained 7-mer cyclic peptide R8-,
      R12-, R18-C

<400> SEQUENCE: 11

Ala Cys Asn Phe Ser Asn Pro Ser Leu Cys
1               5                   10

<210> SEQ ID NO 12
<211> LENGTH: 10
<212> TYPE: PRT
<213> ORGANISM: Artificial Sequence
<220> FEATURE:
<223> OTHER INFORMATION: cysteine-constrained 7-mer cyclic peptide R14-C

<400> SEQUENCE: 12

Ala Cys Pro Phe Ser Asn Pro Ser Met Cys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: cysteine-constrained 7-mer cyclic peptide R16-C

<400> SEQUENCE: 13

Ala Cys Ser Trp Ala Asn Pro Ser Gln Cys
1               5                   10

<210> SEQ ID NO 14
<211> LENGTH: 10
```

```
<212> TYPE: PRT
<213> ORGANISM: Artificial Sequence
<220> FEATURE:
<223> OTHER INFORMATION: cysteine-constrained 7-mer cyclic peptide R17-C

<400> SEQUENCE: 14

Ala Cys Met Phe Ser Asn Pro Ser Leu Cys
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: cysteine-constrained 7-mer cyclic peptide R19-C

<400> SEQUENCE: 15

Ala Cys Pro Phe Ala Asn Pro Ser Met Cys
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: cysteine-constrained 7-mer cyclic peptide R2-C

<400> SEQUENCE: 16

Ala Cys Trp Ala Ser Asn Pro Ser Leu Cys
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: cysteine-constrained 7-mer cyclic peptide R10-C

<400> SEQUENCE: 17

Ala Cys Glu His Ser Asn Pro Ser Leu Cys
 1               5                  10

<210> SEQ ID NO 18
<211> LENGTH: 10
<212> TYPE: PRT
<213> ORGANISM: Artificial Sequence
<220> FEATURE:
<223> OTHER INFORMATION: cysteine-constrained 7-mer cyclic peptide R13-C

<400> SEQUENCE: 18

Ala Cys Trp Ala Ala Asn Pro Ser Met Cys
 1               5                  10

<210> SEQ ID NO 19
<211> LENGTH: 12
<212> TYPE: PRT
<213> ORGANISM: Artificial Sequence
<220> FEATURE:
<223> OTHER INFORMATION: Rituximab mimetope

<400> SEQUENCE: 19

Gln Asp Lys Leu Thr Gln Trp Pro Lys Trp Leu Glu
 1               5                  10

<210> SEQ ID NO 20
<211> LENGTH: 16
<212> TYPE: PRT
```

<213> ORGANISM: Artificial Sequence
<220> FEATURE:
<223> OTHER INFORMATION: QBEnd10-binding epitope

<400> SEQUENCE: 20

Glu Leu Pro Thr Gln Gly Thr Phe Ser Asn Val Ser Thr Asn Val Ser
1               5                   10                  15

<210> SEQ ID NO 21
<211> LENGTH: 136
<212> TYPE: PRT
<213> ORGANISM: Artificial Sequence
<220> FEATURE:
<223> OTHER INFORMATION: Binding domain RQR8

<400> SEQUENCE: 21

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
            20                  25                  30

Ala Lys Pro Thr Thr Thr Ala Cys Pro Tyr Ser Asn Pro Ser Leu Cys
        35                  40                  45

Ser Gly Gly Gly Gly Ser Pro Ala Pro Arg Pro Pro Thr Pro Ala Pro
    50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
            100                 105                 110

Ser Leu Val Ile Thr Leu Tyr Cys Asn His Arg Asn Arg Arg Arg Val
        115                 120                 125

Cys Lys Cys Pro Arg Pro Val Val
        130                 135

<210> SEQ ID NO 22
<211> LENGTH: 79
<212> TYPE: PRT
<213> ORGANISM: Artificial Sequence
<220> FEATURE:
<223> OTHER INFORMATION: Spacer sequence CD8 stalk

<400> SEQUENCE: 22

Pro Ala Pro Arg Pro Pro Thr Pro Ala Pro Thr Ile Ala Ser Gln Pro
1               5                   10                  15

Leu Ser Leu Arg Pro Glu Ala Cys Arg Pro Ala Ala Gly Gly Ala Val
            20                  25                  30

His Thr Arg Gly Leu Asp Phe Ala Cys Asp Ile Tyr Ile Trp Ala Pro
        35                  40                  45

Leu Ala Gly Thr Cys Gly Val Leu Leu Leu Ser Leu Val Ile Thr Leu
    50                  55                  60

Tyr Cys Asn His Arg Asn Arg Arg Arg Val Cys Lys Cys Pro Arg
65                  70                  75

<210> SEQ ID NO 23
<211> LENGTH: 85
<212> TYPE: PRT
<213> ORGANISM: Artificial Sequence
<220> FEATURE:
<223> OTHER INFORMATION: Spacer sequence CD8 stalk + Linker

```
<400> SEQUENCE: 23

Ser Gly Gly Gly Gly Ser Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr Leu Tyr Cys Asn His Arg Asn Arg Arg Arg Val
65                  70                  75                  80

Cys Lys Cys Pro Arg
                85

<210> SEQ ID NO 24
<211> LENGTH: 25
<212> TYPE: PRT
<213> ORGANISM: Artificial Sequence
<220> FEATURE:
<223> OTHER INFORMATION: Spacer sequence GPI signal sequence

<400> SEQUENCE: 24

Ala Ser Ser Asn Ile Ser Gly Gly Ile Phe Leu Phe Phe Val Ala Asn
1               5                   10                  15

Ala Ile Ile His Leu Phe Cys Phe Ser
            20                  25

<210> SEQ ID NO 25
<211> LENGTH: 7
<212> TYPE: PRT
<213> ORGANISM: Artificial Sequence
<220> FEATURE:
<223> OTHER INFORMATION: chain-break sequence

<400> SEQUENCE: 25

Ser Gly Gly Gly Ser Asp Pro
1               5

<210> SEQ ID NO 26
<211> LENGTH: 6
<212> TYPE: PRT
<213> ORGANISM: Artificial Sequence
<220> FEATURE:
<223> OTHER INFORMATION: serine-glycine linker

<400> SEQUENCE: 26

Ser Gly Gly Gly Gly Ser
1               5

<210> SEQ ID NO 27
<211> LENGTH: 57
<212> TYPE: PRT
<213> ORGANISM: Artificial Sequence
<220> FEATURE:
<223> OTHER INFORMATION: RD-PRO transmembrane domain and endodomain

<400> SEQUENCE: 27

Tyr Leu Leu Pro Leu Leu Gly Pro Leu Leu Thr Leu Leu Leu Ile Leu
1               5                   10                  15

Thr Ile Gly Pro Cys Val Phe Ser Arg Leu Met Ala Phe Ile Asn Asp
            20                  25                  30

Arg Leu Asn Val Ser Gln Asn Tyr Pro Ile Val Gln Gln Tyr Gln Ala
```

```
                    35                  40                  45
Leu Lys Ala Glu Glu Ala Gln Asp
    50                  55

<210> SEQ ID NO 28
<211> LENGTH: 6
<212> TYPE: PRT
<213> ORGANISM: Artificial Sequence
<220> FEATURE:
<223> OTHER INFORMATION: thrombin cleavage site

<400> SEQUENCE: 28

Leu Val Pro Arg Gly Ser
1               5

<210> SEQ ID NO 29
<211> LENGTH: 20
<212> TYPE: PRT
<213> ORGANISM: Artificial Sequence
<220> FEATURE:
<223> OTHER INFORMATION: signal peptide

<400> SEQUENCE: 29

Met Glu Thr Asp Thr Leu Leu Leu Trp Val Leu Leu Leu Trp Val Pro
1               5                  10                  15

Gly Ser Thr Gly
            20

<210> SEQ ID NO 30
<211> LENGTH: 21
<212> TYPE: PRT
<213> ORGANISM: Artificial Sequence
<220> FEATURE:
<223> OTHER INFORMATION: signal peptide

<400> SEQUENCE: 30

Met Gly Thr Ser Leu Leu Cys Trp Met Ala Leu Cys Leu Leu Gly Ala
1               5                  10                  15

Asp His Ala Asp Gly
            20

<210> SEQ ID NO 31
<211> LENGTH: 619
<212> TYPE: PRT
<213> ORGANISM: Artificial Sequence
<220> FEATURE:
<223> OTHER INFORMATION: RQR8 tagging of RD114 SU

<400> SEQUENCE: 31

Met Lys Leu Pro Thr Gly Met Val Ile Leu Cys Ser Leu Ile Ile Val
1               5                  10                  15

Arg Ala Cys Pro Tyr Ser Asn Pro Ser Leu Cys Ser Gly Gly Gly Gly
            20                  25                  30

Ser Glu Leu Pro Thr Gln Gly Thr Phe Ser Asn Val Ser Thr Asn Val
        35                  40                  45

Ser Pro Ala Lys Pro Thr Thr Thr Ala Cys Pro Tyr Ser Asn Pro Ser
    50                  55                  60

Leu Cys Ser Gly Gly Gly Gly Ser Gly Phe Asp Asp Pro Arg Lys Ala
65                  70                  75                  80

Ile Ala Leu Val Gln Lys Gln His Gly Lys Pro Cys Glu Cys Ser Gly
                85                  90                  95

Gly Gln Val Ser Glu Ala Pro Pro Asn Ser Ile Gln Gln Val Thr Cys
```

```
            100                 105                 110
Pro Gly Lys Thr Ala Tyr Leu Met Thr Asn Gln Lys Trp Lys Cys Arg
            115                 120                 125

Val Thr Pro Lys Asn Leu Thr Pro Ser Gly Gly Glu Leu Gln Asn Cys
            130                 135             140

Pro Cys Asn Thr Phe Gln Asp Ser Met His Ser Ser Cys Tyr Thr Glu
145                 150                 155                 160

Tyr Arg Gln Cys Arg Ala Asn Asn Lys Thr Tyr Tyr Thr Ala Thr Leu
                165                 170                 175

Leu Lys Ile Arg Ser Gly Ser Leu Asn Glu Val Gln Ile Leu Gln Asn
                180                 185                 190

Pro Asn Gln Leu Leu Gln Ser Pro Cys Arg Gly Ser Ile Asn Gln Pro
            195                 200                 205

Val Cys Trp Ser Ala Thr Ala Pro Ile His Ile Ser Asp Gly Gly Gly
            210                 215                 220

Pro Leu Asp Thr Lys Arg Val Trp Thr Val Gln Lys Arg Leu Glu Gln
225                 230                 235                 240

Ile His Lys Ala Met His Pro Glu Leu Gln Tyr His Pro Leu Ala Leu
                245                 250                 255

Pro Lys Val Arg Asp Asp Leu Ser Leu Asp Ala Arg Thr Phe Asp Ile
            260                 265                 270

Leu Asn Thr Thr Phe Arg Leu Leu Gln Met Ser Asn Phe Ser Leu Ala
            275                 280                 285

Gln Asp Cys Trp Leu Cys Leu Lys Leu Gly Thr Pro Thr Pro Leu Ala
            290                 295                 300

Ile Pro Thr Pro Ser Leu Thr Tyr Ser Leu Ala Asp Ser Leu Ala Asn
305                 310                 315                 320

Ala Ser Cys Gln Ile Ile Pro Pro Leu Leu Val Gln Pro Met Gln Phe
                325                 330                 335

Ser Asn Ser Ser Cys Leu Ser Ser Pro Phe Ile Asn Asp Thr Glu Gln
            340                 345                 350

Ile Asp Leu Gly Ala Val Thr Phe Thr Asn Cys Thr Ser Val Ala Asn
            355                 360                 365

Val Ser Ser Pro Leu Cys Ala Leu Asn Gly Ser Val Phe Leu Cys Gly
            370                 375                 380

Asn Asn Met Ala Tyr Thr Tyr Leu Pro Gln Asn Trp Thr Gly Leu Cys
385                 390                 395                 400

Val Gln Ala Ser Leu Leu Pro Asp Ile Asp Ile Ile Pro Gly Asp Glu
                405                 410                 415

Pro Val Pro Ile Pro Ala Ile Asp His Tyr Ile His Arg Pro Lys Arg
            420                 425                 430

Ala Val Gln Phe Ile Pro Leu Leu Ala Gly Leu Gly Ile Thr Ala Ala
            435                 440                 445

Phe Thr Thr Gly Ala Thr Gly Leu Gly Val Ser Val Thr Gln Tyr Thr
            450                 455                 460

Lys Leu Ser His Gln Leu Ile Ser Asp Val Gln Val Leu Ser Gly Thr
465                 470                 475                 480

Ile Gln Asp Leu Gln Asp Gln Val Asp Ser Leu Ala Glu Val Val Leu
                485                 490                 495

Gln Asn Arg Arg Gly Leu Asp Leu Leu Thr Ala Glu Gln Gly Gly Ile
            500                 505                 510

Cys Leu Ala Leu Gln Glu Lys Cys Cys Phe Tyr Ala Asn Lys Ser Gly
            515                 520                 525
```

```
Ile Val Arg Asn Lys Ile Arg Thr Leu Gln Glu Glu Leu Gln Lys Arg
    530                 535                 540

Arg Glu Ser Leu Ala Ser Asn Pro Leu Trp Thr Gly Leu Gln Gly Phe
545                 550                 555                 560

Leu Pro Tyr Leu Pro Leu Leu Gly Pro Leu Leu Thr Leu Leu
                565                 570                 575

Ile Leu Thr Ile Gly Pro Cys Val Phe Ser Arg Leu Met Ala Phe Ile
            580                 585                 590

Asn Asp Arg Leu Asn Val Ser Gln Asn Tyr Pro Ile Val Gln Gln Tyr
                595                 600                 605

Gln Ala Leu Lys Ala Glu Glu Ala Gln Asp
    610                 615

<210> SEQ ID NO 32
<211> LENGTH: 619
<212> TYPE: PRT
<213> ORGANISM: Artificial Sequence
<220> FEATURE:
<223> OTHER INFORMATION: RQR tagging of RD114 TM

<400> SEQUENCE: 32

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gly Gln Val Ser Glu Ala
        35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Asn Leu
65                  70                  75                  80

Thr Pro Ser Gly Gly Glu Leu Gln Asn Cys Pro Cys Asn Thr Phe Gln
                85                  90                  95

Asp Ser Met His Ser Ser Cys Tyr Thr Glu Tyr Arg Gln Cys Arg Ala
            100                 105                 110

Asn Asn Lys Thr Tyr Tyr Thr Ala Thr Leu Leu Lys Ile Arg Ser Gly
        115                 120                 125

Ser Leu Asn Glu Val Gln Ile Leu Gln Asn Pro Asn Gln Leu Leu Gln
    130                 135                 140

Ser Pro Cys Arg Gly Ser Ile Asn Gln Pro Val Cys Trp Ser Ala Thr
145                 150                 155                 160

Ala Pro Ile His Ile Ser Asp Gly Gly Gly Pro Leu Asp Thr Lys Arg
                165                 170                 175

Val Trp Thr Val Gln Lys Arg Leu Glu Gln Ile His Lys Ala Met His
            180                 185                 190

Pro Glu Leu Gln Tyr His Pro Leu Ala Leu Pro Lys Val Arg Asp Asp
        195                 200                 205

Leu Ser Leu Asp Ala Arg Thr Phe Asp Ile Leu Asn Thr Thr Phe Arg
    210                 215                 220

Leu Leu Gln Met Ser Asn Phe Ser Leu Ala Gln Asp Cys Trp Leu Cys
225                 230                 235                 240

Leu Lys Leu Gly Thr Pro Thr Pro Leu Ala Ile Pro Thr Pro Ser Leu
                245                 250                 255

Thr Tyr Ser Leu Ala Asp Ser Leu Ala Asn Ala Ser Cys Gln Ile Ile
            260                 265                 270
```

```
Pro Pro Leu Leu Val Gln Pro Met Gln Phe Ser Asn Ser Ser Cys Leu
        275                 280                 285
Ser Ser Pro Phe Ile Asn Asp Thr Glu Gln Ile Asp Leu Gly Ala Val
290                 295                 300
Thr Phe Thr Asn Cys Thr Ser Val Ala Asn Val Ser Ser Pro Leu Cys
305                 310                 315                 320
Ala Leu Asn Gly Ser Val Phe Leu Cys Gly Asn Asn Met Ala Tyr Thr
                325                 330                 335
Tyr Leu Pro Gln Asn Trp Thr Gly Leu Cys Val Gln Ala Ser Leu Leu
                340                 345                 350
Pro Asp Ile Asp Ile Ile Pro Gly Asp Glu Pro Val Pro Ile Pro Ala
            355                 360                 365
Ile Asp His Tyr Ile His Arg Pro Lys Arg Cys Pro Tyr Ser Asn Pro
        370                 375                 380
Ser Leu Cys Ser Gly Gly Gly Ser Glu Leu Pro Thr Gln Gly Thr
385                 390                 395                 400
Phe Ser Asn Val Ser Thr Asn Val Ser Pro Ala Lys Pro Thr Thr Thr
                405                 410                 415
Ala Cys Pro Tyr Ser Asn Pro Ser Leu Cys Ser Gly Gly Gly Gly Ser
            420                 425                 430
Ala Val Gln Phe Ile Pro Leu Leu Ala Gly Leu Gly Ile Thr Ala Ala
        435                 440                 445
Phe Thr Thr Gly Ala Thr Gly Leu Gly Val Ser Val Thr Gln Tyr Thr
    450                 455                 460
Lys Leu Ser His Gln Leu Ile Ser Asp Val Gln Val Leu Ser Gly Thr
465                 470                 475                 480
Ile Gln Asp Leu Gln Asp Gln Val Asp Ser Leu Ala Glu Val Val Leu
                485                 490                 495
Gln Asn Arg Arg Gly Leu Asp Leu Leu Thr Ala Glu Gln Gly Gly Ile
            500                 505                 510
Cys Leu Ala Leu Gln Glu Lys Cys Cys Phe Tyr Ala Asn Lys Ser Gly
        515                 520                 525
Ile Val Arg Asn Lys Ile Arg Thr Leu Gln Glu Glu Leu Gln Lys Arg
    530                 535                 540
Arg Glu Ser Leu Ala Ser Asn Pro Leu Trp Thr Gly Leu Gln Gly Phe
545                 550                 555                 560
Leu Pro Tyr Leu Leu Pro Leu Gly Pro Leu Leu Thr Leu Leu Leu
                565                 570                 575
Ile Leu Thr Ile Gly Pro Cys Val Phe Ser Arg Leu Met Ala Phe Ile
            580                 585                 590
Asn Asp Arg Leu Asn Val Ser Gln Asn Tyr Pro Ile Val Gln Gln Tyr
        595                 600                 605
Gln Ala Leu Lys Ala Glu Glu Glu Ala Gln Asp
    610                 615

<210> SEQ ID NO 33
<211> LENGTH: 585
<212> TYPE: PRT
<213> ORGANISM: Artificial Sequence
<220> FEATURE:
<223> OTHER INFORMATION: Flankedcc streptagging of RD114 SU

<400> SEQUENCE: 33

Met Lys Leu Pro Thr Gly Met Val Ile Leu Cys Ser Leu Ile Ile Val
1               5                   10                  15
```

-continued

Arg Ala Glu Cys His Pro Gln Gly Pro Pro Cys Ile Glu Gly Arg Lys
         20                  25                  30

Ser Gly Gly Gly Ser Gly Phe Asp Asp Pro Arg Lys Ala Ile Ala
         35                  40                  45

Leu Val Gln Lys Gln His Gly Lys Pro Cys Glu Cys Ser Gly Gly Gln
50                  55                  60

Val Ser Glu Ala Pro Pro Asn Ser Ile Gln Gln Val Thr Cys Pro Gly
65                  70                  75                  80

Lys Thr Ala Tyr Leu Met Thr Asn Gln Lys Trp Lys Cys Arg Val Thr
                85                  90                  95

Pro Lys Asn Leu Thr Pro Ser Gly Gly Glu Leu Gln Asn Cys Pro Cys
              100                 105                 110

Asn Thr Phe Gln Asp Ser Met His Ser Ser Cys Tyr Thr Glu Tyr Arg
              115                 120                 125

Gln Cys Arg Ala Asn Asn Lys Thr Tyr Tyr Thr Ala Thr Leu Leu Lys
        130                 135                 140

Ile Arg Ser Gly Ser Leu Asn Glu Val Gln Ile Leu Gln Asn Pro Asn
145                 150                 155                 160

Gln Leu Leu Gln Ser Pro Cys Arg Gly Ser Ile Asn Gln Pro Val Cys
                165                 170                 175

Trp Ser Ala Thr Ala Pro Ile His Ile Ser Asp Gly Gly Pro Leu
                180                 185                 190

Asp Thr Lys Arg Val Trp Thr Val Gln Lys Arg Leu Glu Gln Ile His
                195                 200                 205

Lys Ala Met His Pro Glu Leu Gln Tyr His Pro Leu Ala Leu Pro Lys
        210                 215                 220

Val Arg Asp Asp Leu Ser Leu Asp Ala Arg Thr Phe Asp Ile Leu Asn
225                 230                 235                 240

Thr Thr Phe Arg Leu Leu Gln Met Ser Asn Phe Ser Leu Ala Gln Asp
                245                 250                 255

Cys Trp Leu Cys Leu Lys Leu Gly Thr Pro Thr Pro Leu Ala Ile Pro
                260                 265                 270

Thr Pro Ser Leu Thr Tyr Ser Leu Ala Asp Ser Leu Ala Asn Ala Ser
        275                 280                 285

Cys Gln Ile Ile Pro Pro Leu Leu Val Gln Pro Met Gln Phe Ser Asn
        290                 295                 300

Ser Ser Cys Leu Ser Ser Pro Phe Ile Asn Asp Thr Glu Gln Ile Asp
305                 310                 315                 320

Leu Gly Ala Val Thr Phe Thr Asn Cys Thr Ser Val Ala Asn Val Ser
                325                 330                 335

Ser Pro Leu Cys Ala Leu Asn Gly Ser Val Phe Leu Cys Gly Asn Asn
                340                 345                 350

Met Ala Tyr Thr Tyr Leu Pro Gln Asn Trp Thr Gly Leu Cys Val Gln
        355                 360                 365

Ala Ser Leu Leu Pro Asp Ile Asp Ile Ile Pro Gly Asp Glu Pro Val
        370                 375                 380

Pro Ile Pro Ala Ile Asp His Tyr Ile His Arg Pro Lys Arg Ala Val
385                 390                 395                 400

Gln Phe Ile Pro Leu Leu Ala Gly Leu Gly Ile Thr Ala Ala Phe Thr
                405                 410                 415

Thr Gly Ala Thr Gly Leu Gly Val Ser Val Thr Gln Tyr Thr Lys Leu
                420                 425                 430

-continued

```
Ser His Gln Leu Ile Ser Asp Val Gln Val Leu Ser Gly Thr Ile Gln
            435                 440                 445

Asp Leu Gln Asp Gln Val Asp Ser Leu Ala Glu Val Val Leu Gln Asn
450                 455                 460

Arg Arg Gly Leu Asp Leu Leu Thr Ala Glu Gln Gly Gly Ile Cys Leu
465                 470                 475                 480

Ala Leu Gln Glu Lys Cys Cys Phe Tyr Ala Asn Lys Ser Gly Ile Val
                485                 490                 495

Arg Asn Lys Ile Arg Thr Leu Gln Glu Leu Gln Lys Arg Arg Glu
            500                 505                 510

Ser Leu Ala Ser Asn Pro Leu Trp Thr Gly Leu Gln Gly Phe Leu Pro
            515                 520                 525

Tyr Leu Leu Pro Leu Leu Gly Pro Leu Leu Thr Leu Leu Leu Ile Leu
530                 535                 540

Thr Ile Gly Pro Cys Val Phe Ser Arg Leu Met Ala Phe Ile Asn Asp
545                 550                 555                 560

Arg Leu Asn Val Ser Gln Asn Tyr Pro Ile Val Gln Gln Tyr Gln Ala
                565                 570                 575

Leu Lys Ala Glu Glu Ala Gln Asp
            580                 585

<210> SEQ ID NO 34
<211> LENGTH: 585
<212> TYPE: PRT
<213> ORGANISM: Artificial Sequence
<220> FEATURE:
<223> OTHER INFORMATION: Flankedcc streptagging of RD114 TM

<400> SEQUENCE: 34

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gly Gln Val Ser Glu Ala
        35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Asn Leu
65                  70                  75                  80

Thr Pro Ser Gly Gly Glu Leu Gln Asn Cys Pro Cys Asn Thr Phe Gln
                85                  90                  95

Asp Ser Met His Ser Ser Cys Tyr Thr Glu Tyr Arg Gln Cys Arg Ala
            100                 105                 110

Asn Asn Lys Thr Tyr Tyr Thr Ala Thr Leu Leu Lys Ile Arg Ser Gly
        115                 120                 125

Ser Leu Asn Glu Val Gln Ile Leu Gln Asn Pro Asn Gln Leu Leu Gln
    130                 135                 140

Ser Pro Cys Arg Gly Ser Ile Asn Gln Pro Val Cys Trp Ser Ala Thr
145                 150                 155                 160

Ala Pro Ile His Ile Ser Asp Gly Gly Gly Pro Leu Asp Thr Lys Arg
                165                 170                 175

Val Trp Thr Val Gln Lys Arg Leu Glu Gln Ile His Lys Ala Met His
            180                 185                 190

Pro Glu Leu Gln Tyr His Pro Leu Ala Leu Pro Lys Val Arg Asp Asp
        195                 200                 205
```

```
Leu Ser Leu Asp Ala Arg Thr Phe Asp Ile Leu Asn Thr Thr Phe Arg
210                 215                 220

Leu Leu Gln Met Ser Asn Phe Ser Leu Ala Gln Asp Cys Trp Leu Cys
225                 230                 235                 240

Leu Lys Leu Gly Thr Pro Thr Pro Leu Ala Ile Pro Thr Pro Ser Leu
            245                 250                 255

Thr Tyr Ser Leu Ala Asp Ser Leu Ala Asn Ala Ser Cys Gln Ile Ile
        260                 265                 270

Pro Pro Leu Val Gln Pro Met Gln Phe Ser Asn Ser Ser Cys Leu
        275                 280                 285

Ser Ser Pro Phe Ile Asn Asp Thr Glu Gln Ile Asp Leu Gly Ala Val
290                 295                 300

Thr Phe Thr Asn Cys Thr Ser Val Ala Asn Val Ser Ser Pro Leu Cys
305                 310                 315                 320

Ala Leu Asn Gly Ser Val Phe Leu Cys Gly Asn Asn Met Ala Tyr Thr
                325                 330                 335

Tyr Leu Pro Gln Asn Trp Thr Gly Leu Cys Val Gln Ala Ser Leu Leu
            340                 345                 350

Pro Asp Ile Asp Ile Ile Pro Gly Asp Glu Pro Val Pro Ile Pro Ala
            355                 360                 365

Ile Asp His Tyr Ile His Arg Pro Lys Arg Glu Cys His Pro Gln Gly
370                 375                 380

Pro Pro Cys Ile Glu Gly Arg Lys Ser Gly Gly Gly Ser Ala Val
385                 390                 395                 400

Gln Phe Ile Pro Leu Leu Ala Gly Leu Gly Ile Thr Ala Ala Phe Thr
                405                 410                 415

Thr Gly Ala Thr Gly Leu Gly Val Ser Val Thr Gln Tyr Thr Lys Leu
            420                 425                 430

Ser His Gln Leu Ile Ser Asp Val Gln Val Leu Ser Gly Thr Ile Gln
            435                 440                 445

Asp Leu Gln Asp Gln Val Asp Ser Leu Ala Glu Val Val Leu Gln Asn
            450                 455                 460

Arg Arg Gly Leu Asp Leu Leu Thr Ala Glu Gln Gly Gly Ile Cys Leu
465                 470                 475                 480

Ala Leu Gln Glu Lys Cys Cys Phe Tyr Ala Asn Lys Ser Gly Ile Val
                485                 490                 495

Arg Asn Lys Ile Arg Thr Leu Gln Glu Glu Leu Gln Lys Arg Arg Glu
            500                 505                 510

Ser Leu Ala Ser Asn Pro Leu Trp Thr Gly Leu Gln Gly Phe Leu Pro
            515                 520                 525

Tyr Leu Leu Pro Leu Leu Gly Pro Leu Leu Thr Leu Leu Leu Ile Leu
530                 535                 540

Thr Ile Gly Pro Cys Val Phe Ser Arg Leu Met Ala Phe Ile Asn Asp
545                 550                 555                 560

Arg Leu Asn Val Ser Gln Asn Tyr Pro Ile Val Gln Gln Tyr Gln Ala
            565                 570                 575

Leu Lys Ala Glu Glu Glu Ala Gln Asp
            580                 585

<210> SEQ ID NO 35
<211> LENGTH: 15
<212> TYPE: PRT
<213> ORGANISM: Artificial Sequence
<220> FEATURE:
<223> OTHER INFORMATION: Biotin mimicking peptide, long nanotag
```

-continued

<400> SEQUENCE: 35

Asp Val Glu Ala Trp Leu Asp Glu Arg Val Pro Leu Val Glu Thr
1               5                   10                  15

<210> SEQ ID NO 36
<211> LENGTH: 9
<212> TYPE: PRT
<213> ORGANISM: Artificial Sequence
<220> FEATURE:
<223> OTHER INFORMATION: Biotin mimicking peptide, short nanotag

<400> SEQUENCE: 36

Asp Val Glu Ala Trp Leu Gly Ala Arg
1               5

<210> SEQ ID NO 37
<211> LENGTH: 38
<212> TYPE: PRT
<213> ORGANISM: Artificial Sequence
<220> FEATURE:
<223> OTHER INFORMATION: Biotin mimicking peptide, SBP-tag

<400> SEQUENCE: 37

Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 38
<211> LENGTH: 8
<212> TYPE: PRT
<213> ORGANISM: Artificial Sequence
<220> FEATURE:
<223> OTHER INFORMATION: Biotin mimicking peptide, streptag

<400> SEQUENCE: 38

Trp Arg His Pro Gln Phe Gly Gly
1               5

<210> SEQ ID NO 39
<211> LENGTH: 565
<212> TYPE: PRT
<213> ORGANISM: Artificial Sequence
<220> FEATURE:
<223> OTHER INFORMATION: pRDpro amino acid sequence

<400> SEQUENCE: 39

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gly Gln Val Ser Glu Ala
        35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Asn Leu
65                  70                  75                  80

Thr Pro Ser Gly Gly Glu Leu Gln Asn Cys Pro Cys Asn Thr Phe Gln
                85                  90                  95

```
Asp Ser Met His Ser Ser Cys Tyr Thr Glu Tyr Arg Gln Cys Arg Ala
            100                 105                 110

Asn Asn Lys Thr Tyr Tyr Thr Ala Thr Leu Leu Lys Ile Arg Ser Gly
        115                 120                 125

Ser Leu Asn Glu Val Gln Ile Leu Gln Asn Pro Asn Gln Leu Leu Gln
    130                 135                 140

Ser Pro Cys Arg Gly Ser Ile Asn Gln Pro Val Cys Trp Ser Ala Thr
145                 150                 155                 160

Ala Pro Ile His Ile Ser Asp Gly Gly Pro Leu Asp Thr Lys Arg
                165                 170                 175

Val Trp Thr Val Gln Lys Arg Leu Glu Gln Ile His Lys Ala Met His
            180                 185                 190

Pro Glu Leu Gln Tyr His Pro Leu Ala Leu Pro Lys Val Arg Asp Asp
        195                 200                 205

Leu Ser Leu Asp Ala Arg Thr Phe Asp Ile Leu Asn Thr Thr Phe Arg
    210                 215                 220

Leu Leu Gln Met Ser Asn Phe Ser Leu Ala Gln Asp Cys Trp Leu Cys
225                 230                 235                 240

Leu Lys Leu Gly Thr Pro Thr Pro Leu Ala Ile Pro Thr Pro Ser Leu
                245                 250                 255

Thr Tyr Ser Leu Ala Asp Ser Leu Ala Asn Ala Ser Cys Gln Ile Ile
            260                 265                 270

Pro Pro Leu Leu Val Gln Pro Met Gln Phe Ser Asn Ser Ser Cys Leu
        275                 280                 285

Ser Ser Pro Phe Ile Asn Asp Thr Glu Gln Ile Asp Leu Gly Ala Val
    290                 295                 300

Thr Phe Thr Asn Cys Thr Ser Val Ala Asn Val Ser Ser Pro Leu Cys
305                 310                 315                 320

Ala Leu Asn Gly Ser Val Phe Leu Cys Gly Asn Asn Met Ala Tyr Thr
                325                 330                 335

Tyr Leu Pro Gln Asn Trp Thr Gly Leu Cys Val Gln Ala Ser Leu Leu
            340                 345                 350

Pro Asp Ile Asp Ile Ile Pro Gly Asp Glu Pro Val Pro Ile Pro Ala
        355                 360                 365

Ile Asp His Tyr Ile His Arg Pro Lys Arg Ala Val Gln Phe Ile Pro
    370                 375                 380

Leu Leu Ala Gly Leu Gly Ile Thr Ala Ala Phe Thr Thr Gly Ala Thr
385                 390                 395                 400

Gly Leu Gly Val Ser Val Thr Gln Tyr Thr Lys Leu Ser His Gln Leu
                405                 410                 415

Ile Ser Asp Val Gln Val Leu Ser Gly Thr Ile Gln Asp Leu Gln Asp
            420                 425                 430

Gln Val Asp Ser Leu Ala Glu Val Val Leu Gln Asn Arg Arg Gly Leu
        435                 440                 445

Asp Leu Leu Thr Ala Glu Gln Gly Gly Ile Cys Leu Ala Leu Gln Glu
    450                 455                 460

Lys Cys Cys Phe Tyr Ala Asn Lys Ser Gly Ile Val Arg Asn Lys Ile
465                 470                 475                 480

Arg Thr Leu Gln Glu Glu Leu Gln Lys Arg Arg Glu Ser Leu Ala Ser
                485                 490                 495

Asn Pro Leu Trp Thr Gly Leu Gln Gly Phe Leu Pro Tyr Leu Leu Pro
            500                 505                 510

Leu Leu Gly Pro Leu Leu Thr Leu Leu Leu Ile Leu Thr Ile Gly Pro
```

```
            515                 520                 525
Cys Val Phe Ser Arg Leu Met Ala Phe Ile Asn Asp Arg Leu Asn Val
            530                 535                 540

Ser Gln Asn Tyr Pro Ile Val Gln Gln Tyr Gln Ala Leu Lys Ala Glu
545                 550                 555                 560

Glu Glu Ala Gln Asp
                565

<210> SEQ ID NO 40
<211> LENGTH: 564
<212> TYPE: PRT
<213> ORGANISM: Artificial Sequence
<220> FEATURE:
<223> OTHER INFORMATION: RD114 amino acid sequence

<400> SEQUENCE: 40

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gly Gln Val Ser Glu Ala
        35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Ile Ser
65                  70                  75                  80

Pro Ser Gly Gly Glu Leu Gln Asn Cys Pro Cys Asn Thr Phe Gln Asp
                85                  90                  95

Ser Met His Ser Ser Cys Tyr Thr Glu Tyr Arg Gln Cys Arg Arg Ile
            100                 105                 110

Asn Lys Thr Tyr Tyr Thr Ala Thr Leu Leu Lys Ile Arg Ser Gly Ser
        115                 120                 125

Leu Asn Glu Val Gln Ile Leu Gln Asn Pro Asn Gln Leu Leu Gln Ser
    130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Pro Leu Asp Thr Lys Arg Val
                165                 170                 175

Trp Thr Val Gln Lys Arg Leu Glu Gln Ile His Lys Ala Met Thr Pro
            180                 185                 190

Glu Leu Gln Tyr His Pro Leu Ala Leu Pro Lys Val Arg Asp Asp Leu
        195                 200                 205

Ser Leu Asp Ala Arg Thr Phe Asp Ile Leu Asn Thr Thr Phe Arg Leu
    210                 215                 220

Leu Gln Met Ser Asn Phe Ser Leu Ala Gln Asp Cys Trp Leu Cys Leu
225                 230                 235                 240

Lys Leu Gly Thr Pro Thr Pro Leu Ala Ile Pro Thr Pro Ser Leu Thr
                245                 250                 255

Tyr Ser Leu Ala Asp Ser Leu Ala Asn Ala Ser Cys Gln Ile Ile Pro
            260                 265                 270

Pro Leu Leu Val Gln Pro Met Gln Phe Ser Asn Ser Ser Cys Leu Ser
        275                 280                 285

Ser Pro Phe Ile Asn Asp Thr Glu Gln Ile Asp Leu Gly Ala Val Thr
    290                 295                 300

Phe Thr Asn Cys Thr Ser Val Ala Asn Val Ser Ser Pro Leu Cys Ala
```

```
                305                 310                 315                 320
Leu Asn Gly Ser Val Phe Leu Cys Gly Asn Asn Met Ala Tyr Thr Tyr
                325                 330                 335

Leu Pro Gln Asn Trp Thr Arg Leu Cys Val Gln Ala Ser Leu Leu Pro
                340                 345                 350

Asp Ile Asp Ile Asn Pro Gly Asp Glu Pro Val Pro Ile Pro Ala Ile
                355                 360                 365

Asp His Tyr Ile His Arg Pro Lys Arg Ala Val Gln Phe Ile Pro Leu
                370                 375                 380

Leu Ala Gly Leu Gly Ile Thr Ala Ala Phe Thr Thr Gly Ala Thr Gly
385                 390                 395                 400

Leu Gly Val Ser Val Thr Gln Tyr Thr Lys Leu Ser His Gln Leu Ile
                405                 410                 415

Ser Asp Val Gln Val Leu Ser Gly Thr Ile Gln Asp Leu Gln Asp Gln
                420                 425                 430

Val Asp Ser Leu Ala Glu Val Val Leu Gln Asn Arg Arg Gly Leu Asp
                435                 440                 445

Leu Leu Thr Ala Glu Gln Gly Gly Ile Cys Leu Ala Leu Gln Glu Lys
                450                 455                 460

Cys Cys Phe Tyr Ala Asn Lys Ser Gly Ile Val Arg Asn Lys Ile Arg
465                 470                 475                 480

Thr Leu Gln Glu Glu Leu Gln Lys Arg Arg Glu Ser Leu Ala Thr Asn
                485                 490                 495

Pro Leu Trp Thr Gly Leu Gln Gly Phe Leu Pro Tyr Leu Leu Pro Leu
                500                 505                 510

Leu Gly Pro Leu Leu Thr Leu Leu Leu Ile Leu Thr Ile Gly Pro Cys
                515                 520                 525

Val Phe Ser Arg Leu Met Ala Phe Ile Asn Asp Arg Leu Asn Val Val
                530                 535                 540

His Ala Met Val Leu Ala Gln Gln Tyr Gln Ala Leu Lys Ala Glu Glu
545                 550                 555                 560

Glu Ala Gln Asp

<210> SEQ ID NO 41
<211> LENGTH: 4
<212> TYPE: PRT
<213> ORGANISM: Artificial Sequence
<220> FEATURE:
<223> OTHER INFORMATION: Furin cleavage site

<400> SEQUENCE: 41

Arg Pro Lys Arg
1

<210> SEQ ID NO 42
<211> LENGTH: 21
<212> TYPE: PRT
<213> ORGANISM: Artificial Sequence
<220> FEATURE:
<223> OTHER INFORMATION: signal peptide

<400> SEQUENCE: 42

Met Gly Thr Ser Leu Leu Cys Trp Met Ala Leu Cys Leu Leu Gly Ala
1               5                   10                  15

Asp His Ala Asp Ala
            20
```

```
<210> SEQ ID NO 43
<211> LENGTH: 14
<212> TYPE: PRT
<213> ORGANISM: Artificial Sequence
<220> FEATURE:
<223> OTHER INFORMATION: Biotin mimicking peptide sequence

<400> SEQUENCE: 43

Glu Cys His Pro Gln Gly Pro Pro Cys Ile Glu Gly Arg Lys
1               5                   10

<210> SEQ ID NO 44
<211> LENGTH: 88
<212> TYPE: PRT
<213> ORGANISM: Artificial Sequence
<220> FEATURE:
<223> OTHER INFORMATION: CD8 stalk with linker sequence

<400> SEQUENCE: 44

Ser Gly Gly Gly Gly Ser Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
                20                  25                  30

Ala Ala Gly Gly Ala Val His Thr Arg Gly Leu Asp Phe Ala Cys Asp
            35                  40                  45

Ile Tyr Ile Trp Ala Pro Leu Ala Gly Thr Cys Gly Val Leu Leu Leu
        50                  55                  60

Ser Leu Val Ile Thr Leu Tyr Cys Asn His Arg Asn Arg Arg Arg Val
65                  70                  75                  80

Cys Lys Cys Pro Arg Pro Val Val
                85

<210> SEQ ID NO 45
<211> LENGTH: 31
<212> TYPE: PRT
<213> ORGANISM: Artificial Sequence
<220> FEATURE:
<223> OTHER INFORMATION: GPI anchor with linker

<400> SEQUENCE: 45

Ser Gly Gly Gly Gly Ser Ala Ser Ser Asn Ile Ser Gly Gly Ile Phe
1               5                   10                  15

Leu Phe Phe Val Ala Asn Ala Ile Ile His Leu Phe Cys Phe Ser
                20                  25                  30

<210> SEQ ID NO 46
<211> LENGTH: 20
<212> TYPE: PRT
<213> ORGANISM: Artificial Sequence
<220> FEATURE:
<223> OTHER INFORMATION: CD8 linker

<400> SEQUENCE: 46

Ser Gly Gly Gly Gly Ser Pro Ala Pro Arg Pro Pro Thr Pro Ala Pro
1               5                   10                  15

Thr Ile Ala Ser
                20

<210> SEQ ID NO 47
<211> LENGTH: 123
<212> TYPE: PRT
<213> ORGANISM: Artificial Sequence
<220> FEATURE:
<223> OTHER INFORMATION: Flankedccstreptag-L8 amino acid sequence
```

<400> SEQUENCE: 47

```
Met Gly Thr Ser Leu Leu Cys Trp Met Ala Leu Cys Leu Leu Gly Ala
1               5                   10                  15

Asp His Ala Asp Ala Glu Cys His Pro Gln Gly Pro Pro Cys Ile Glu
            20                  25                  30

Gly Arg Lys Ser Gly Gly Gly Ser Pro Ala Pro Arg Pro Pro Thr
        35                  40                  45

Pro Ala Pro Thr Ile Ala Ser Gln Pro Leu Ser Leu Arg Pro Glu Ala
        50                  55                  60

Cys Arg Pro Ala Ala Gly Gly Ala Val His Thr Arg Gly Leu Asp Phe
65                  70                  75                  80

Ala Cys Asp Ile Tyr Ile Trp Ala Pro Leu Ala Gly Thr Cys Gly Val
                85                  90                  95

Leu Leu Leu Ser Leu Val Ile Thr Leu Tyr Cys Asn His Arg Asn Arg
            100                 105                 110

Arg Arg Val Cys Lys Cys Pro Arg Pro Val Val
            115                 120
```

<210> SEQ ID NO 48
<211> LENGTH: 339
<212> TYPE: PRT
<213> ORGANISM: Artificial Sequence
<220> FEATURE:
<223> OTHER INFORMATION: Glutathione S-transferases-L8 amino acid
      sequence

<400> SEQUENCE: 48

```
Met Gly Thr Ser Leu Leu Cys Trp Met Ala Leu Cys Leu Leu Gly Ala
1               5                   10                  15

Asp His Ala Asp Ala Met Ser Pro Ile Leu Gly Tyr Trp Lys Ile Lys
            20                  25                  30

Gly Leu Val Gln Pro Thr Arg Leu Leu Leu Glu Tyr Leu Glu Glu Lys
        35                  40                  45

Tyr Glu Glu His Leu Tyr Glu Arg Asp Glu Gly Asp Lys Trp Arg Asn
    50                  55                  60

Lys Lys Phe Glu Leu Gly Leu Glu Phe Pro Asn Leu Pro Tyr Tyr Ile
65                  70                  75                  80

Asp Gly Asp Val Lys Leu Thr Gln Ser Met Ala Ile Ile Arg Tyr Ile
                85                  90                  95

Ala Asp Lys His Asn Met Leu Gly Gly Cys Pro Lys Glu Arg Ala Glu
            100                 105                 110

Ile Ser Met Leu Glu Gly Ala Val Leu Asp Ile Arg Tyr Gly Val Ser
        115                 120                 125

Arg Ile Ala Tyr Ser Lys Asp Phe Glu Thr Leu Lys Val Asp Phe Leu
    130                 135                 140

Ser Lys Leu Pro Glu Met Leu Lys Met Phe Glu Asp Arg Leu Cys His
145                 150                 155                 160

Lys Thr Tyr Leu Asn Gly Asp His Val Thr His Pro Asp Phe Met Leu
                165                 170                 175

Tyr Asp Ala Leu Asp Val Val Leu Tyr Met Asp Pro Met Cys Leu Asp
            180                 185                 190

Ala Phe Pro Lys Leu Val Cys Phe Lys Lys Arg Ile Glu Ala Ile Pro
        195                 200                 205

Gln Ile Asp Lys Tyr Leu Lys Ser Ser Lys Tyr Ile Ala Trp Pro Leu
    210                 215                 220
```

```
Gln Gly Trp Gln Ala Thr Phe Gly Gly Gly Asp His Pro Pro Lys Ser
225                 230                 235                 240

Asp Leu Glu Val Leu Phe Gln Gly Pro Leu Gly Ser Gly Gly Gly Gly
                245                 250                 255

Ser Pro Ala Pro Arg Pro Pro Thr Pro Ala Pro Thr Ile Ala Ser Gln
            260                 265                 270

Pro Leu Ser Leu Arg Pro Glu Ala Cys Arg Pro Ala Ala Gly Gly Ala
        275                 280                 285

Val His Thr Arg Gly Leu Asp Phe Ala Cys Asp Ile Tyr Ile Trp Ala
    290                 295                 300

Pro Leu Ala Gly Thr Cys Gly Val Leu Leu Leu Ser Leu Val Ile Thr
305                 310                 315                 320

Leu Tyr Cys Asn His Arg Asn Arg Arg Val Cys Lys Cys Pro Arg
                325                 330                 335

Pro Val Val
```

<210> SEQ ID NO 49
<211> LENGTH: 157
<212> TYPE: PRT
<213> ORGANISM: Artificial Sequence
<220> FEATURE:
<223> OTHER INFORMATION: RTXep-QBEND10ep-RTXep-L8 amino acid sequence

<400> SEQUENCE: 49

```
Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Val Cys Lys Cys Pro Arg Pro Val Val
145                 150                 155
```

<210> SEQ ID NO 50
<211> LENGTH: 116
<212> TYPE: PRT
<213> ORGANISM: Artificial Sequence
<220> FEATURE:
<223> OTHER INFORMATION: H6-L8 amino acid sequence

<400> SEQUENCE: 50

```
Met Gly Thr Ser Leu Leu Cys Trp Met Ala Leu Cys Leu Leu Gly Ala
1               5                   10                  15

Asp His Ala Asp Ala Ser His His His His His Ser Gly Gly Gly
            20                  25                  30
```

```
Gly Ser Pro Ala Pro Arg Pro Thr Pro Ala Pro Thr Ile Ala Ser
        35                  40                  45

Gln Pro Leu Ser Leu Arg Pro Glu Ala Cys Arg Pro Ala Ala Gly Gly
    50                  55                  60

Ala Val His Thr Arg Gly Leu Asp Phe Ala Cys Asp Ile Tyr Ile Trp
65                  70                  75                  80

Ala Pro Leu Ala Gly Thr Cys Gly Val Leu Leu Leu Ser Leu Val Ile
                85                  90                  95

Thr Leu Tyr Cys Asn His Arg Asn Arg Arg Val Cys Lys Cys Pro
                100                 105                 110

Arg Pro Val Val
        115

<210> SEQ ID NO 51
<211> LENGTH: 15
<212> TYPE: PRT
<213> ORGANISM: Artificial Sequence
<220> FEATURE:
<223> OTHER INFORMATION: Biotin mimicking peptide, Flankedccstreptag-GPI

<400> SEQUENCE: 51

Glu Cys His Pro Gln Gly Pro Pro Cys Ile Glu Gly Arg Lys Ser
1               5                   10                  15

<210> SEQ ID NO 52
<211> LENGTH: 37
<212> TYPE: PRT
<213> ORGANISM: Artificial Sequence
<220> FEATURE:
<223> OTHER INFORMATION: Biotin mimiking peptide, ccstreptag-d8-x2-GPI

<400> SEQUENCE: 52

Cys His Pro Pro Gln Gly Pro Pro Cys Ser Gly Gly Gly Ser Pro
1               5                   10                  15

Ala Pro Arg Pro Pro Thr Pro Ala Pro Thr Ile Ala Ser Cys His Pro
            20                  25                  30

Gln Gly Pro Pro Cys
        35
```

METHOD AND MEANS FOR PURIFYING RETROVIRAL VECTORS

FIELD OF THE INVENTION

The present invention relates to the field of retroviral vectors. In particular the invention relates to methods for the production of lentiviral vectors, producer cells and tagging proteins for use in such methods.

BACKGROUND TO THE INVENTION

Retroviral vectors are relevant for a range of applications, including gene therapy. However, progress in lentiviral gene therapy, for example, has been hampered by the requirement for production of purified lentiviral vectors with high titre.

Lentiviral vectors are typically generated by a packaging cell which releases vector particles into the supernatant. Since lentiviral vectors are labile, subsequent purification methods must use physiological (or non-harsh) conditions as much as possible to maximize recovery of the vector. Further, the methodology needs to be scalable and cost-effective.

Currently, lentiviral particles are usually purified from supernatant by ultracentrifugation. This is a laborious process, which only provides a 40% viral recovery and cannot be easily scaled. Other methods for the purification have been explored, for example ultrafiltration—which provides a 50% recovery using a 750 kda membrane, low density gradient centrifugation or anion exchange chromatography. All of these methods are cumbersome and laborious and relatively unproven. Additionally, these methods result in the concentration of envelope proteins as well as other cellular components that hinder the infectivity of the viral titre.

Affinity chromatography may be used as a single-step capture method for the generic recovery of viral vectors by exploiting streptavidin and biotin interactions. Nesbeth et al. (Molecular Therapy 2006, 13, 814-822) engineered a novel human 293T based packaging cell line BL15, which metabolically produces spontaneously biotin-tagged lentiviral vectors requiring only biotin in the culture medium. This metabolic biotinylation technology facilitates highly efficient affinity-mediated paramagnetic-particle and chromatographic capture of viral particles.

A similar system has been described for adenovirus (Parrott et al. (2003) Mol. Ther. 8:688-700), in which the fiber capsid protein is genetically fused to a biotin acceptor peptide, which is metabolically biotinylated during vector production by the endogenous biotin ligase in 293 cells.

However, the value of such biotinylation systems for purification of viral vectors in manufacturing is limited for two main reasons: since the affinity of biotin to streptavidin is very high, subsequent removal of the virus from the streptavidin matrix is difficult and requires harsh conditions. Further, since these methods require presence of biotin, residual free biotin competes with the streptavidin matrix for binding (Nesbeth et al. 2006 (as above); Williams et al. (2005) Biotechnology and Bioengineering 89: 783-787; and Williams et al. (2005) Journal of Chromatography B 820: 111-119).

There have also been various reports of strategies to aid purification of recombinant viral vectors by engineering the viral envelope protein to include some kind of tag.

WO2007/095201 describes a viral vector comprising a recombinant viral envelope protein consisting of a rhabdovirus viral envelope, such as VSV-G, engineered with a heterologous polypeptide. The heterologous polypeptide is cloned between the SU and TM unit of the envelope. Peptide-tagged-viral particles are subsequently purified by metal ion affinity chromatography.

WO2014/121005 describes a viral vector comprising an epitope-tagged viral envelope whereby the epitopes, CD118, V5 or HA, are cloned after the signal peptide or after the proline rich region (PRR) of viral envelope glycoproteins. Subsequent purification of the supernatant relies on a centrifugation upon harvesting of epitope-tagged viral particles followed by incubation with antibodies against the three epitopes. Purified particles are then eluted by adding the antigen ie the epitope of the antibodies.

Ye et al (2004, J. Virol. 78:9820-9827) engineered a metal binding peptide-tagged MLV envelope by incorporating the peptide into a part of hypervariable region of the viral protein. Subsequent viral purification then involved immobilized metal affinity chromatography.

WO2004/000220 describes tagging the spike protein of VSV-G by insertion of a His-6 peptide tag. Virus then may be isolated a purified by column affinity chromatography or sedimentation with magnetic beads.

A disadvantage of such systems is that insertion of a tagging protein into the reading frame of a viral envelop protein can disrupt the functional integrity of the envelope protein and negatively impact viral titer.

This issue is illustrated by studies aimed at genetically engineering the viral envelope glycoprotein for cell-specific viral transduction. The viral envelope glycoprotein of Moloney leukemia virus (MLV) is the most commonly altered envelope for targeted transduction with modifications including: peptide insertion in pre-folded domains; expression of peptides as additional domains; and peptides fused directly to the transmembrane part of the envelope.

Even though some of these studies generated correctly folded chimeric envelopes that were be able to bind its specific receptor on target cells, most N-terminally substituted chimeric envelopes studied to date have either had very low viral incorporation or absence of transduction of target cells. For example, gammaretroviral vectors with envelope proteins modified to the stromal cell derived factor 1-alpha (Katane et al., 2002 EMBO Rep. 3, 899-904. doi: 10.1093/embo-reports/kvf179) or an integrin binding peptide (Wu et al., 2010 Cancer Res. 70, 9549-9553. doi: 10.1158/0008-5472.CAN-10-1760) were shown to have poor transduction efficiencies.

The genetic engineering of viral envelope proteins such as MLV, VSV-G and RD114 therefore remains a technical challenge for the field. This is due to the delicate interaction between the binding and fusion domains. Their dependent activities, when altered by peptide insertions, seem to inhibit infection and in turn negatively impact viral titer. This is true for methods involving altering envelope glycoproteins in order to tag vector for purification as well as methods involving altering envelope glycoproteins in order to enable cell-specific viral transduction.

Thus there is a need for methods for producing and purifying retroviral vectors which are not associated with these disadvantages.

A. Schematic diagram of the amino acid sequences of the six Streptavidin-binding tags on a CD8 stalk. These constructs co-express the green fluorescent protein (eGFP) via an internal ribosome entry sequence (IRES) downstream of the first open reading frames. B. The constructs were transfected into HEK 293T cells and stained with Streptavidin-APC 48 hours post-transfection and analysed by flow-cytometry. Binding of streptavidin (y-axis) is plotted against eGFP signal. Difference in streptavidin binding of the different constructs is clearly seen.

Figure 2:
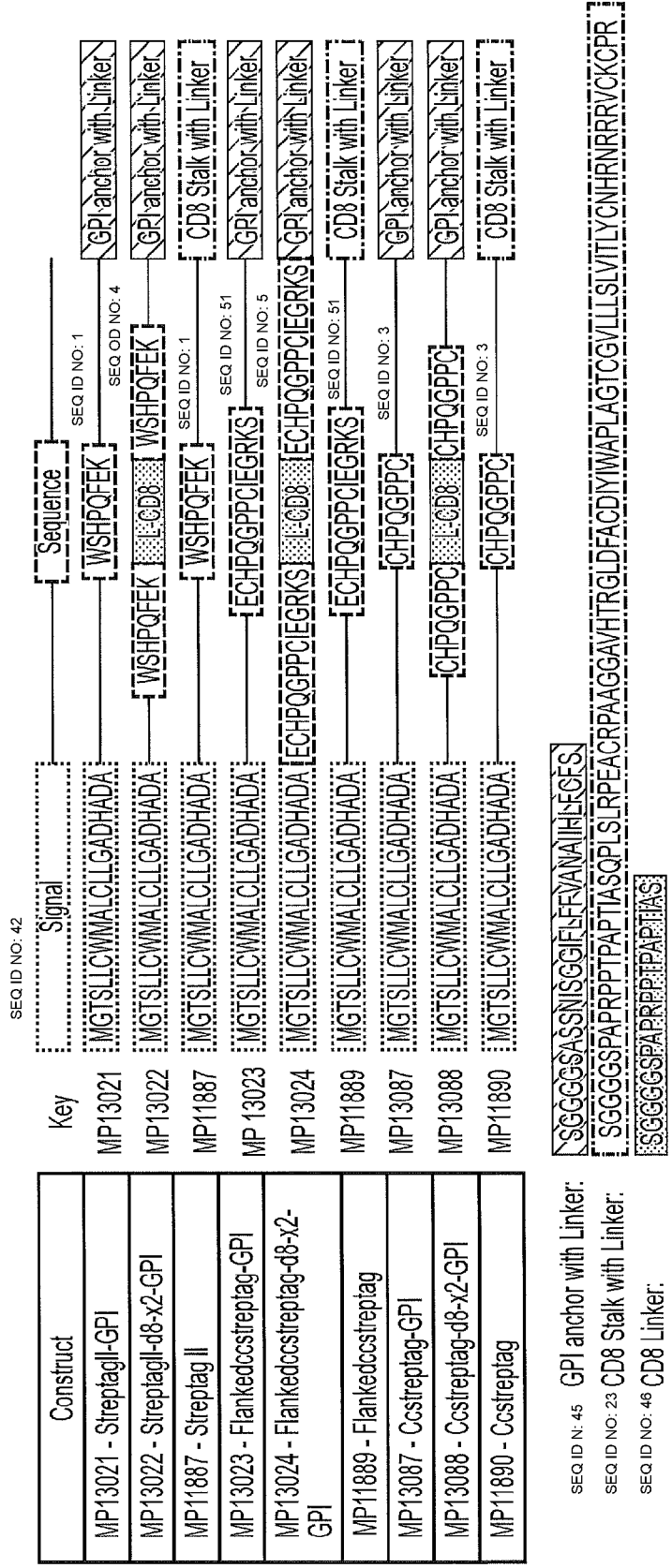

FIG. 2: Annotation of StreptagII, Flankedccstreptag and ccstretag epitopes in three different formats. The constructs all have an amino-terminal signal peptides, then one or two copies of a streptavidin binding peptide. In case of two streptavidin binding peptides, the peptides are separated by a portion of the CD8 stalk. Next, the constructs are either attached to the CD8 stalk, transmembrane and a short endodomain, or else are connected to a GPI signal. All the constructs co-express eGFP via an IRES downstream of the open reading frame of the tagging protein.

Figure 3:
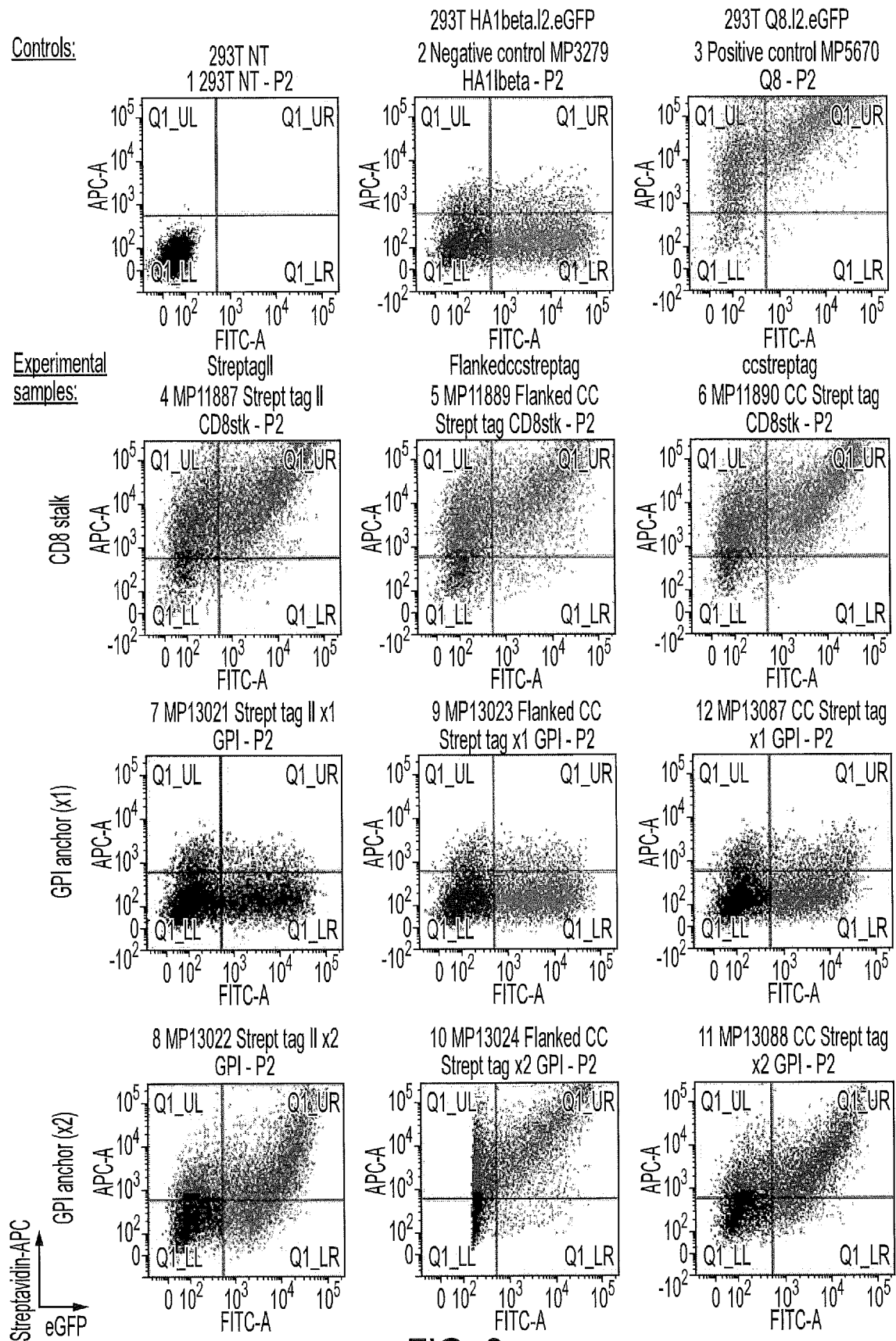

FIG. 3: Transfection of 293T cells with StreptagII, Flankedccstreptag and ccstretag epitopes in three different formats shown in FIG. 2. 293T cells were also transfected with an irrelevant protein (HA1-TCR beta) co-expressed with eGFP as a negative control. Some cells were co-expressed with Q8.I2.eGFP and stained with a primary antibody Qbend10-Biotin followed by a secondary antibody Streptavidin-APC as a positive control. Tags were expressed on either a CD8 stalk, a GPI anchor (×1) with one open reading frame or with a GPI anchor (×2) with two copies of the open reading frame. 293T cells transfected with the tagging proteins were stained with Streptavidin APC. The cells were all analysed by flow-cytometry and Streptavidin APC binding (y-axis) is plotted against eGFP signal (x-axis). Of the GPI-anchored tags, only those with two copies of the streptavidin binding peptide seemed to bind streptavidin.

FIG. 4: Sorting of K562 cells transduced with Flankedccstreptag-D8-x2-GPI and -L8 sorting with streptavidin beads.

Transduced K562 were close to 100% positive for the transgenes after transduction. Positive cells were mixed with non-transduced (NT) K562 pre-sorting. The mixture was incubated with both streptavidin dynabeads (Life technologies, Cat. No. 65601) and streptavidin-microbeads (Miltenyi, Cat. No. 130-048-101) as per manufacturer protocol. The sorted cellular fraction was collected as well as flow-through fraction for both protocols. Sorting was assessed by streptavidin-APC staining and for eGFP positive cell populations 9 days post sorting by flow cytometry.

Figure 5:
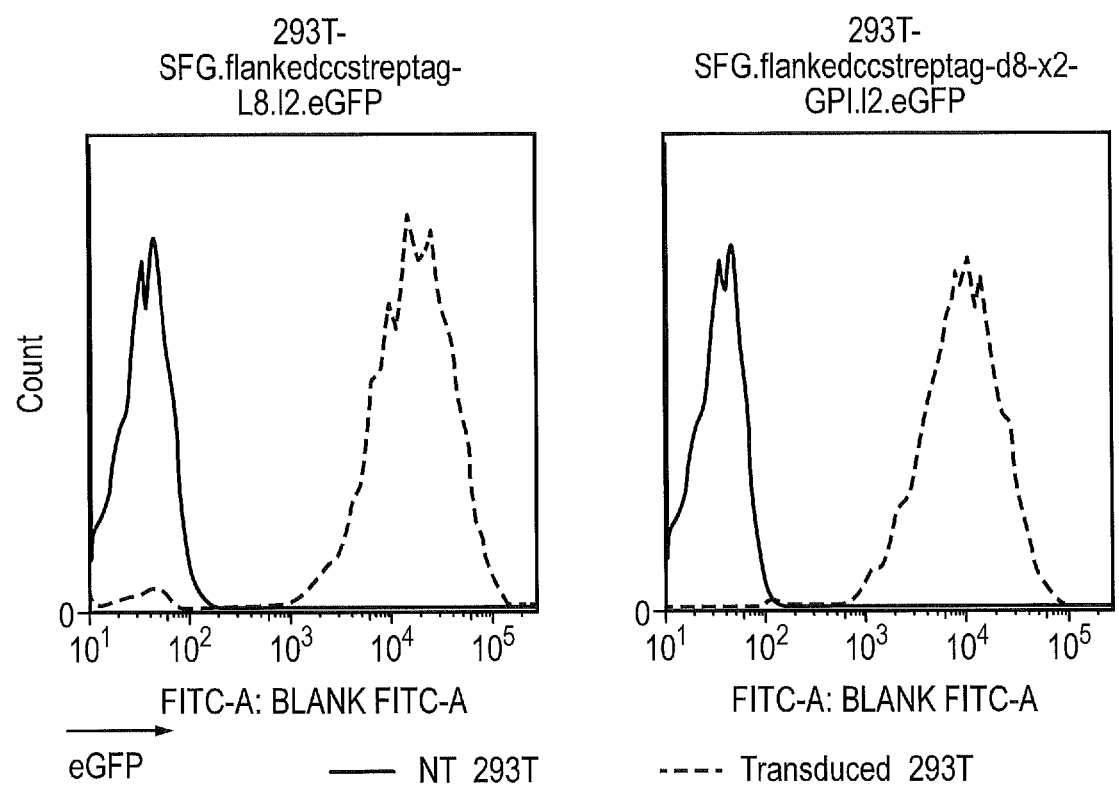

FIG. 5: Retroviral transduction of 293T cells to stably express flankedccstreptag epitope constructs.

Expression of the transgene is demonstrated by detection of eGFP by flow-cytometry. eGFP fluorescence is shown as a histogram overlaid on signal from non-transduced 293T cells. The 293T cells are 100% positive for the transgenes.

Figure 6:
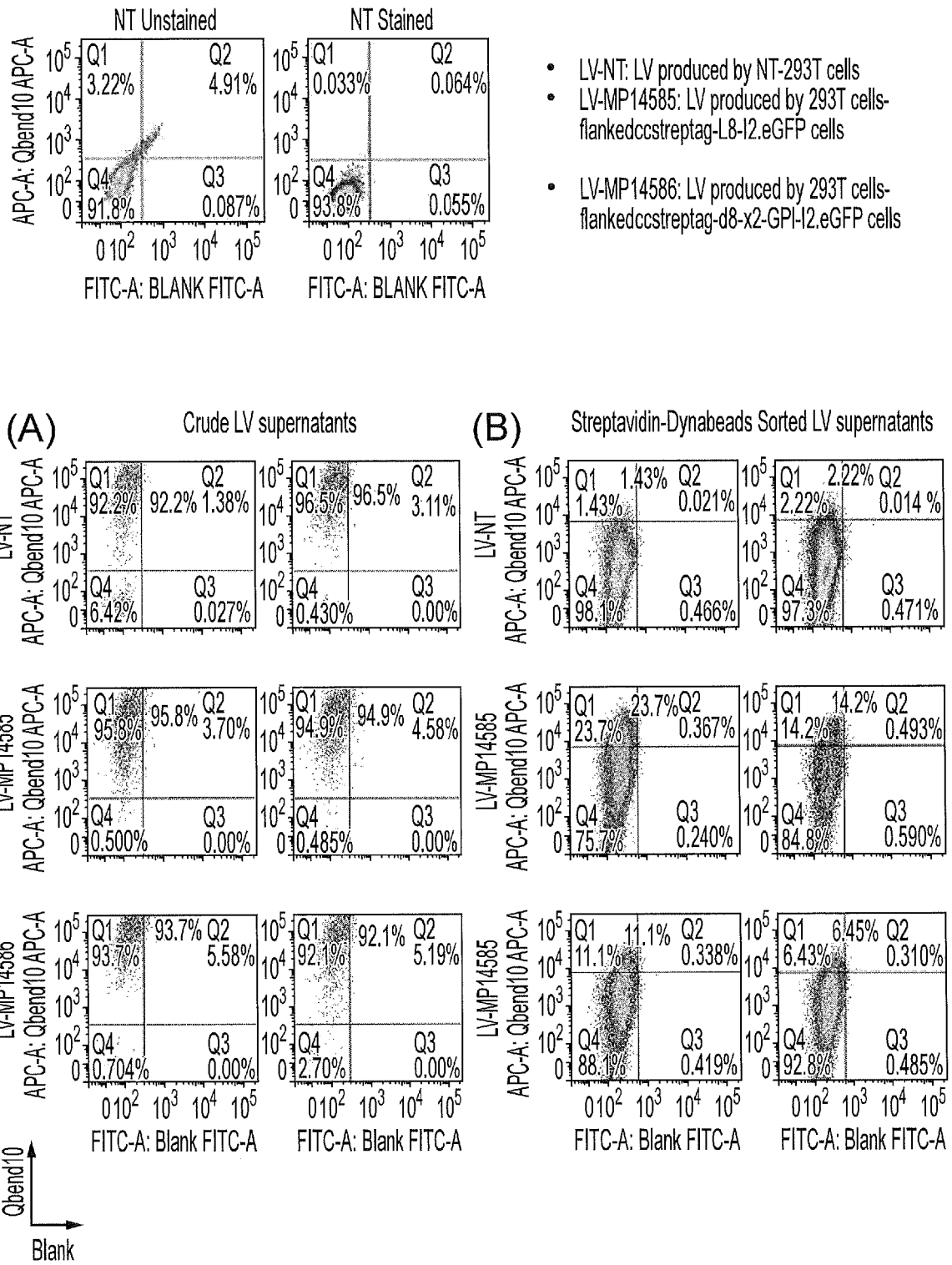

FIG. 6: Lentiviral transduction of NT-293T cells with epitope-tagged-lentiviral supernatant sorted with streptavidin-beads.

VSV-G pseudotyped LV particles were produced from 293T cells expressing either flankedccstreptag-L8 (LV-MP14585) or flankedccstreptag-d8-x2-GPI (LV-MP14586) on their surface in a second generation packaging system. Supernatants were separated into a crude fraction (Crude LV; which represent non-purified supernatant) and a purified fraction were LV produced from 293T cells-flankedccstreptag-L8-I2.eGFP and from 293T cells-flankedccstreptag-d8-x2-I2-eGFP were incubated with Streptavidin-Dynabeads for 2 hours at 4 C with rotation. Beads-LV mixture was then placed on a magnetic rack causing the beads to be immobilized. After washing the beads-virus complex with PBS 5 times, complexes were resuspended in cold media as Sorted LV (left). As a negative control non-tagged-LV was incubated with the beads (LV-NT). The transgene encodes a chimeric antigen receptor with a marker gene that can be stained using Qbend10-APC antibody. Supernatants were used to transduce NT-293T cells in the presence of polybrene 10 mg/mL. Performed in duplicate.

FIG. 7: Amino acid sequence of flankedccstreptag, glutathione-s-transferase, RQR8 and polyhistidine-tag (H6) epitope on CD8 stalks Amino acid sequences of the different constructs are shown with the different component segments annotated.

Figure 8:
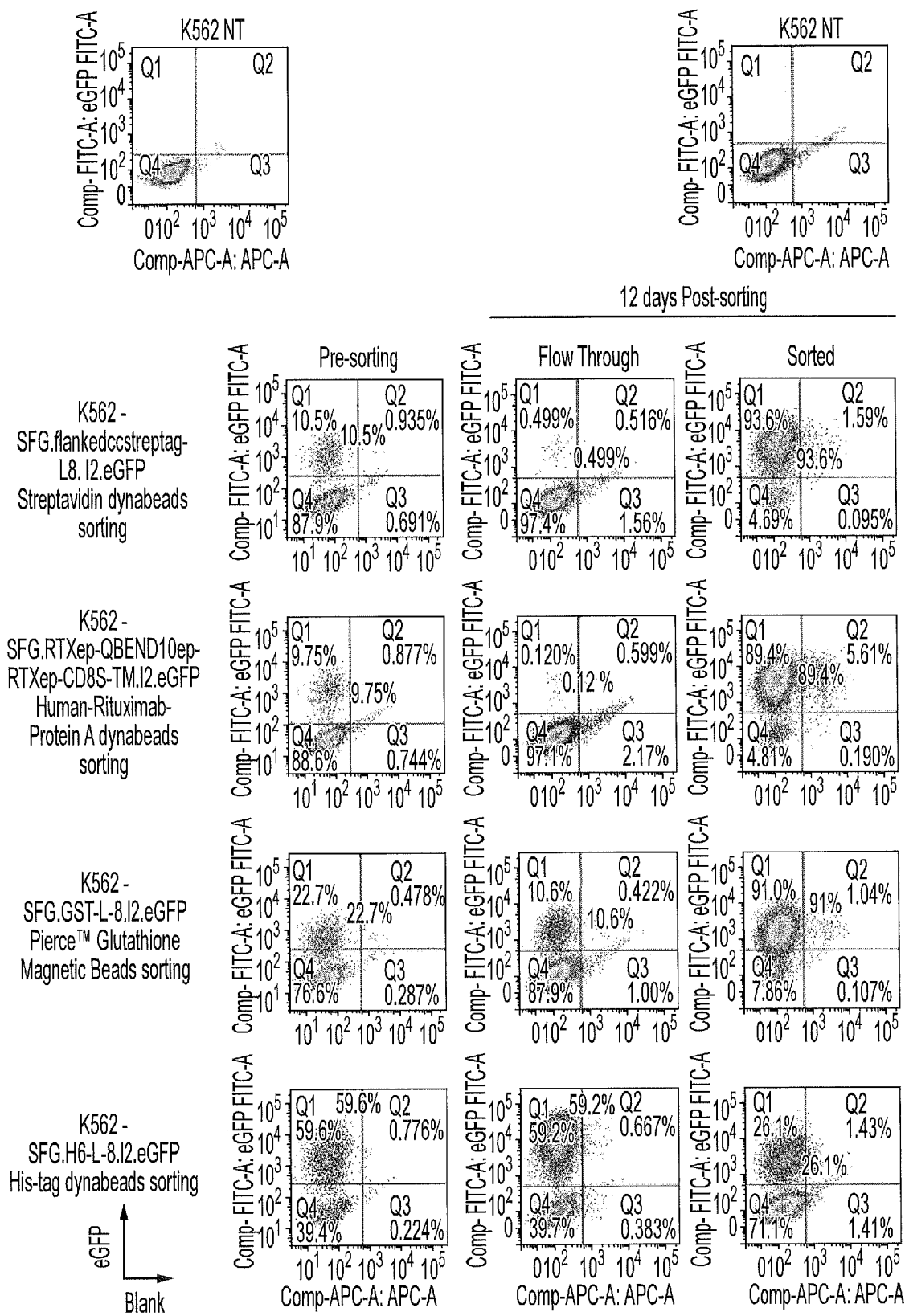

FIG. 8: Viral purification by sorting K562 cells with respective beads using GST, RQR8 and His-tag epitopes.

K562 cells were retrovirally transduced with the four constructs individually. Subsequently cell populations were sorted with their respective beads as per manufacturer protocol. Protein-A Dynabeads were previously incubated with clinical grade human-rituximab over-night at 4 C and washed 5× with PBS to remove any unbound rituximab before adding it to the cells. Sorted fractions were collected as well as the flow through for all sorting. Fractions were assessed for positive cells based on eGFP expression by flow cytometery with a blank channel to account for auto fluorescence from dead cells.

Figure 9:
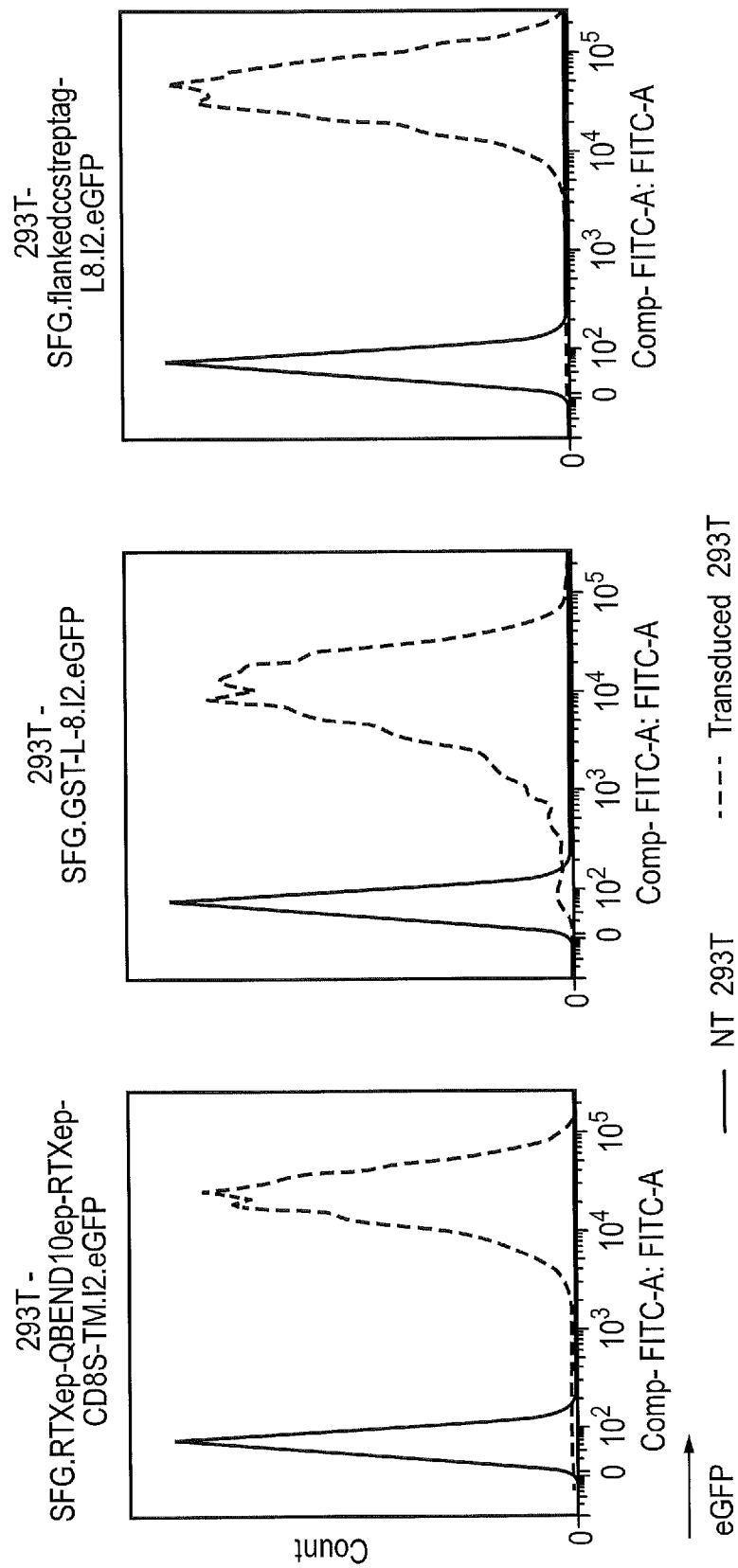

FIG. 9: Retroviral transduction of 293T cells with RQR8, GST and flankedccstreptag epitope constructs.

Transgene expression is confirmed by detecting eGFP fluorescence by flow-cytometry. A histogram showing eGFP fluorescence is shown for each 293T cell line overlaid on the signal from non-transduced 293T-cells.

Figure 10:
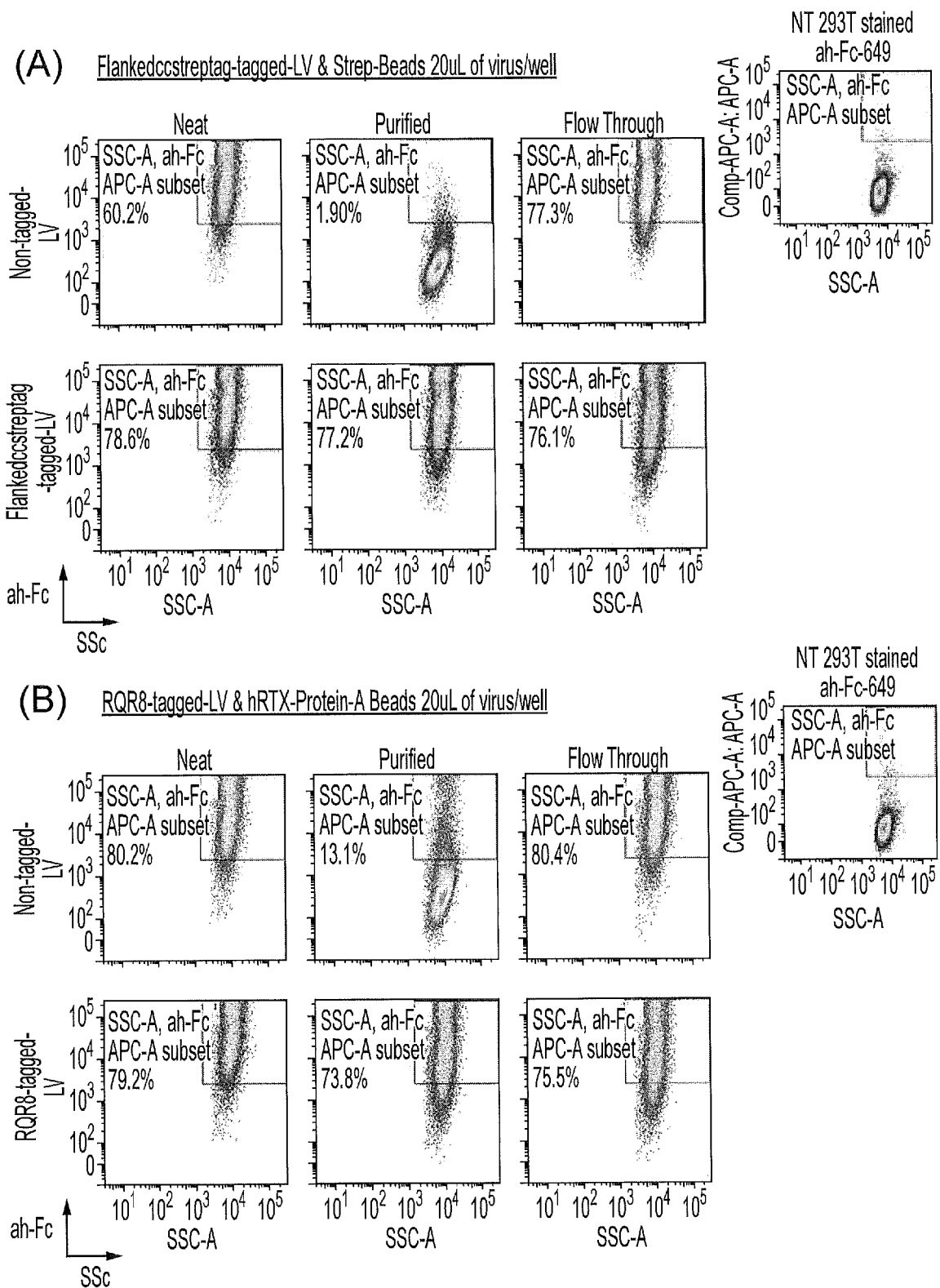
Figure 10:
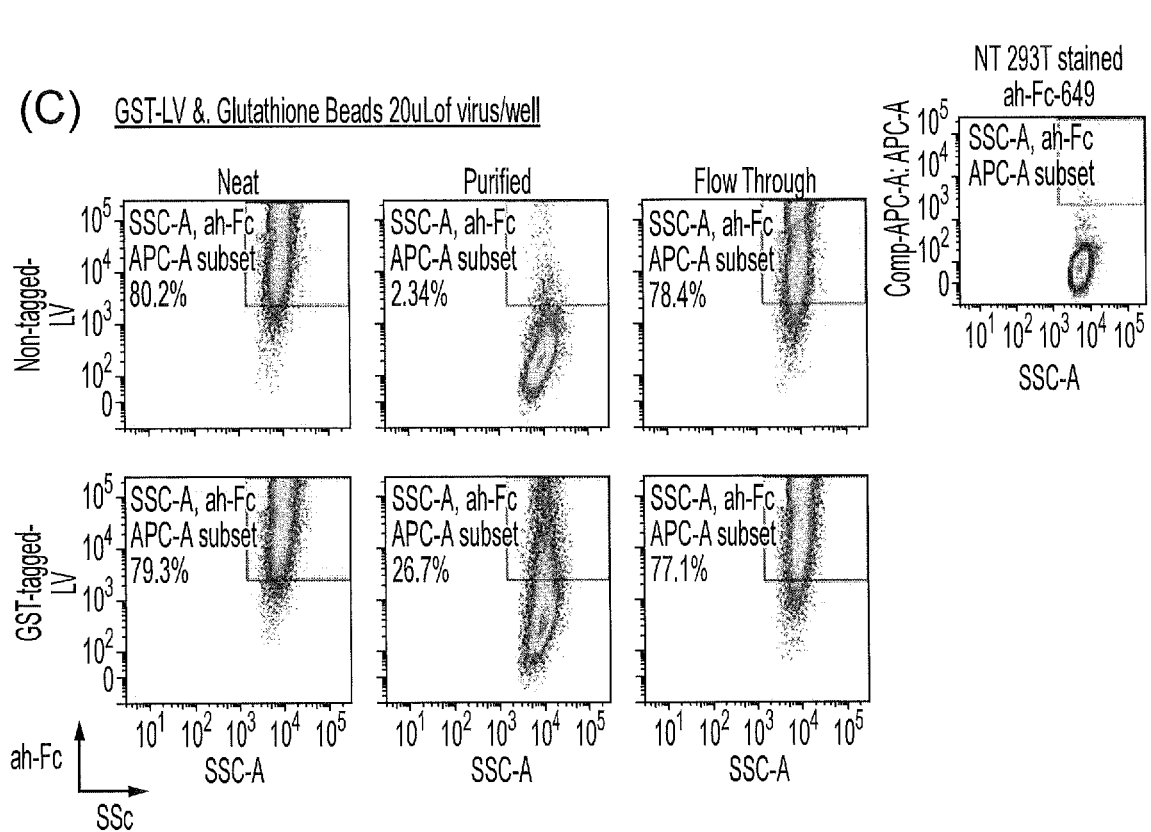

FIG. 10: Purification of tagged LV purification from cellular supernatant and subsequent 293T-NT cell transduction.

VSV-G pseudotyped LV particles encoding a chimeric antigen receptor (CAR) with a human-Fc spacer were produced from 293T cells expressing the synthetic tags on their surface (Flankedccstreptag (A), RQR8 (B) and GST (C)) in a second generation packaging system. Supernatants were separated into a crude fraction (Neat; which represent non-purified supernatant) and a purified fraction were flankedccstreptag-tagged LV, RQR8-tagged LV and GST-tagged LV were incubated with Streptavidin-Dynabeads, human Rituximab (hRTX) pre-incubated with Protein-A Dynabeads (o/n and washed to remove any unbound hRTX) and Glutathione-beads, respectively for 2 hours at 4° C. with rotation. Beads-LV mixture was then placed on a magnetic rack and once the beads immobilized, media were collected as Flow-Through fractions. After washing the beads-virus complex with PBS 5 times, complexes were resuspended in cold media as Purified fractions (middle columns). As a negative control non-tagged-LV was incubated with Streptavidin-Beads, hRTX-Protein-A-Beads and Glutathione-beads. Target cells were transduced with the test vector and stained 120 hrs-post transduction with a fluorescently conjugated antibody which detects the chimeric antigen receptor and analysed by flow-cytometry. A dot-plot of CAR expression versus side-scatter is shown for all conditions.

Figure 11:
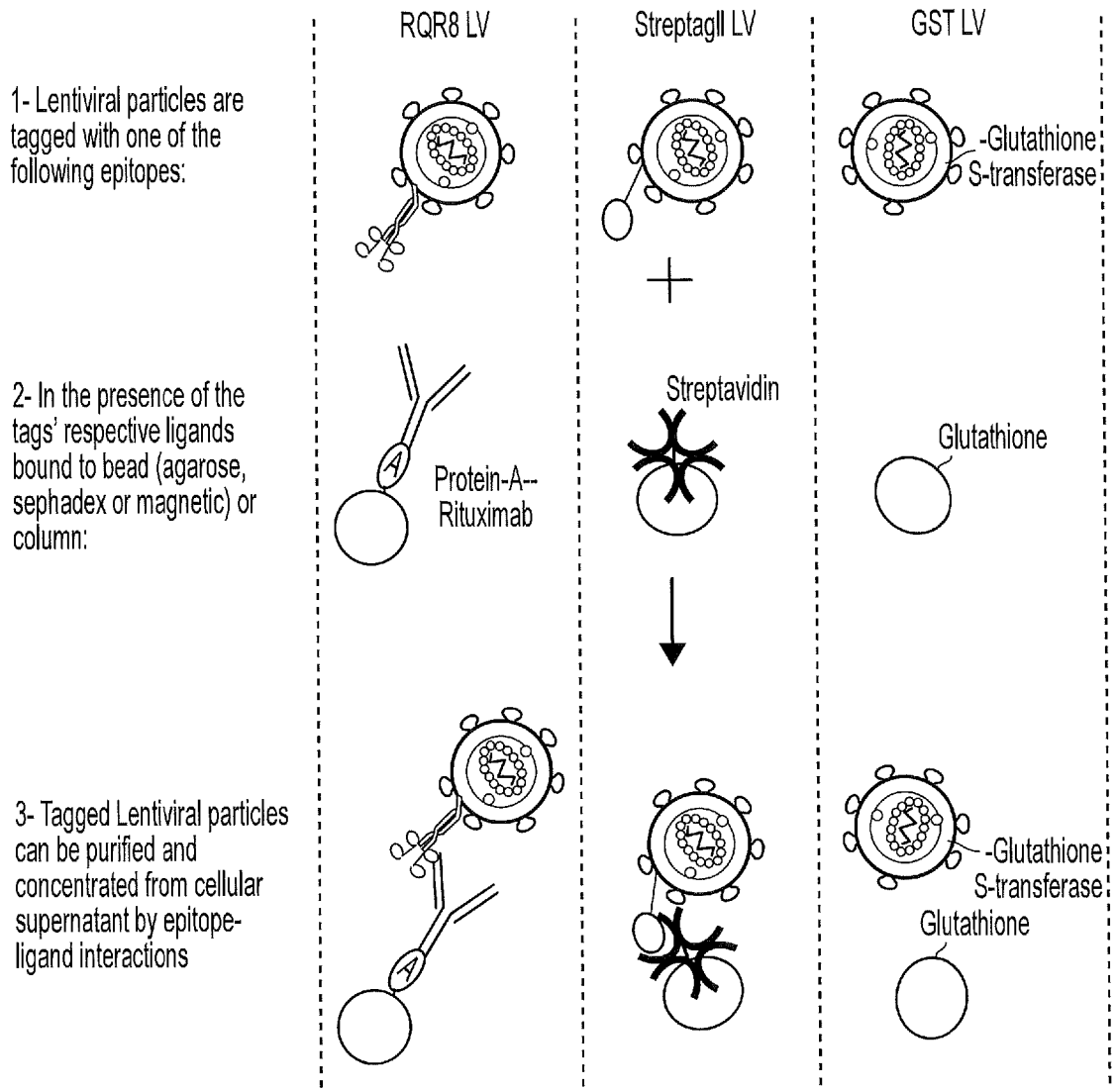

FIG. 11: Schematic representation of tagged-LV particles purified by their respective ligand. In this process, viral particles bound to either of these tags can be both purified from crude supernatant and concentrated to an arbitrary fold using a wide variety of ligand-bound bead.

Figure 12:
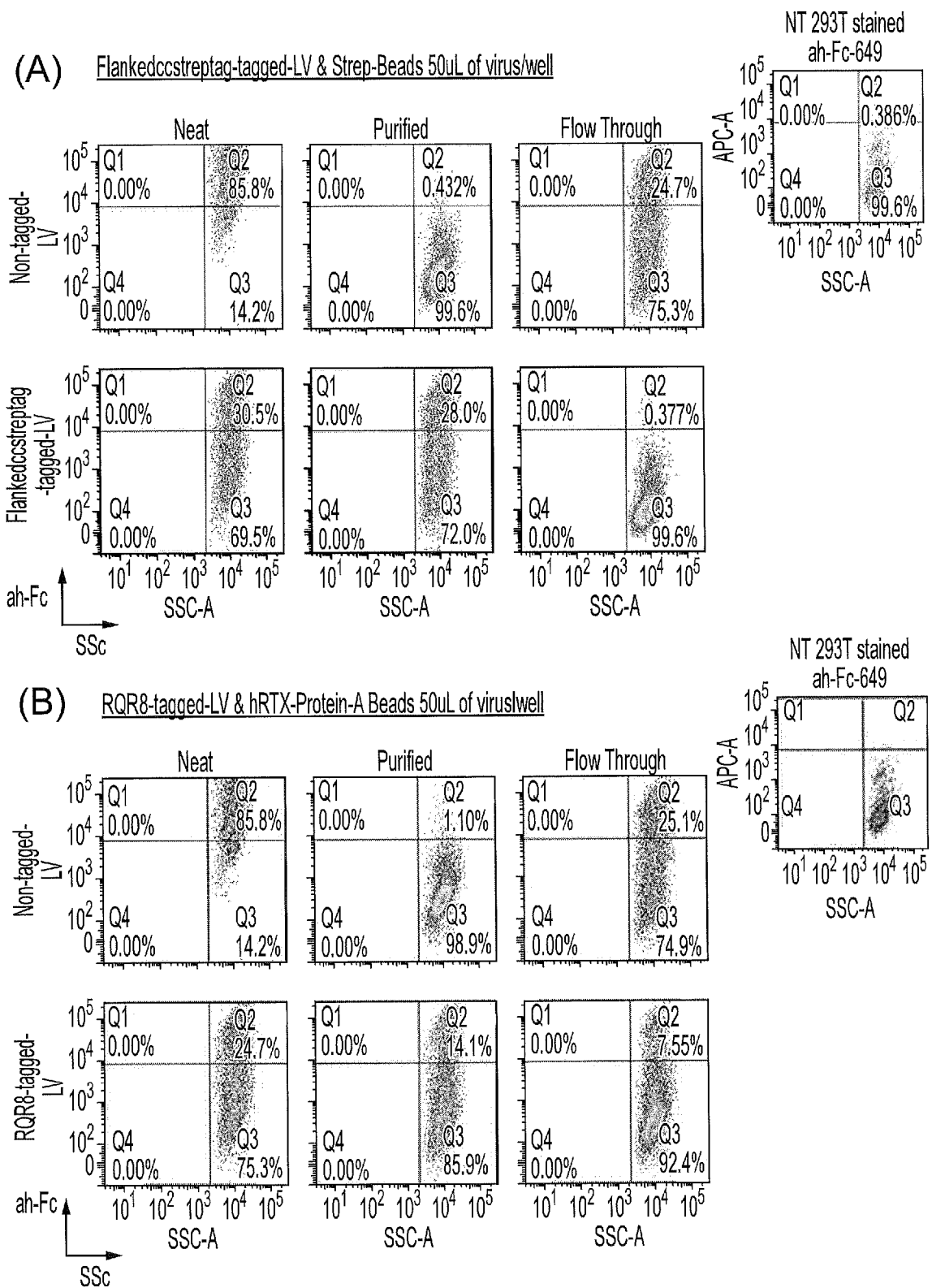

FIG. 12: RDpro-pseudotyped tagged LV purification from cellular supernatant and subsequent 293T cells transduction.

RDpro pseudotyped LV particles encoding a chimeric antigen receptor (CAR) were produced from 293T cells expressing the synthetic tags on their surface (Flankedccstreptag (A) and RQR8 (B)). Supernatant were treated exactly as in FIG. 10, separated into a crude fraction (Neat; which represent non-purified supernatant) and a purified fraction were flankedccstreptagl-tagged LV and RQR8-tagged LV, which were incubated with Streptavidin-Dynabeads and human Rituximab (pre-incubated with Protein-A Dynabeads), respectively. Flow through were collected upon magnetic immobilisation of the beads. As a negative control non-tagged-LV was incubated with both Strep-Beads and hRTX-Protein-A-Beads. 293T cells were transduced with the test LV. These target cells were stained 120 hrs-post transduction with a fluorescently conjugated antibody which detects the CAR and analysed by flow-cytometry. CAR-expression vs side-scatter is shown on a dot-plot.

Figure 13:
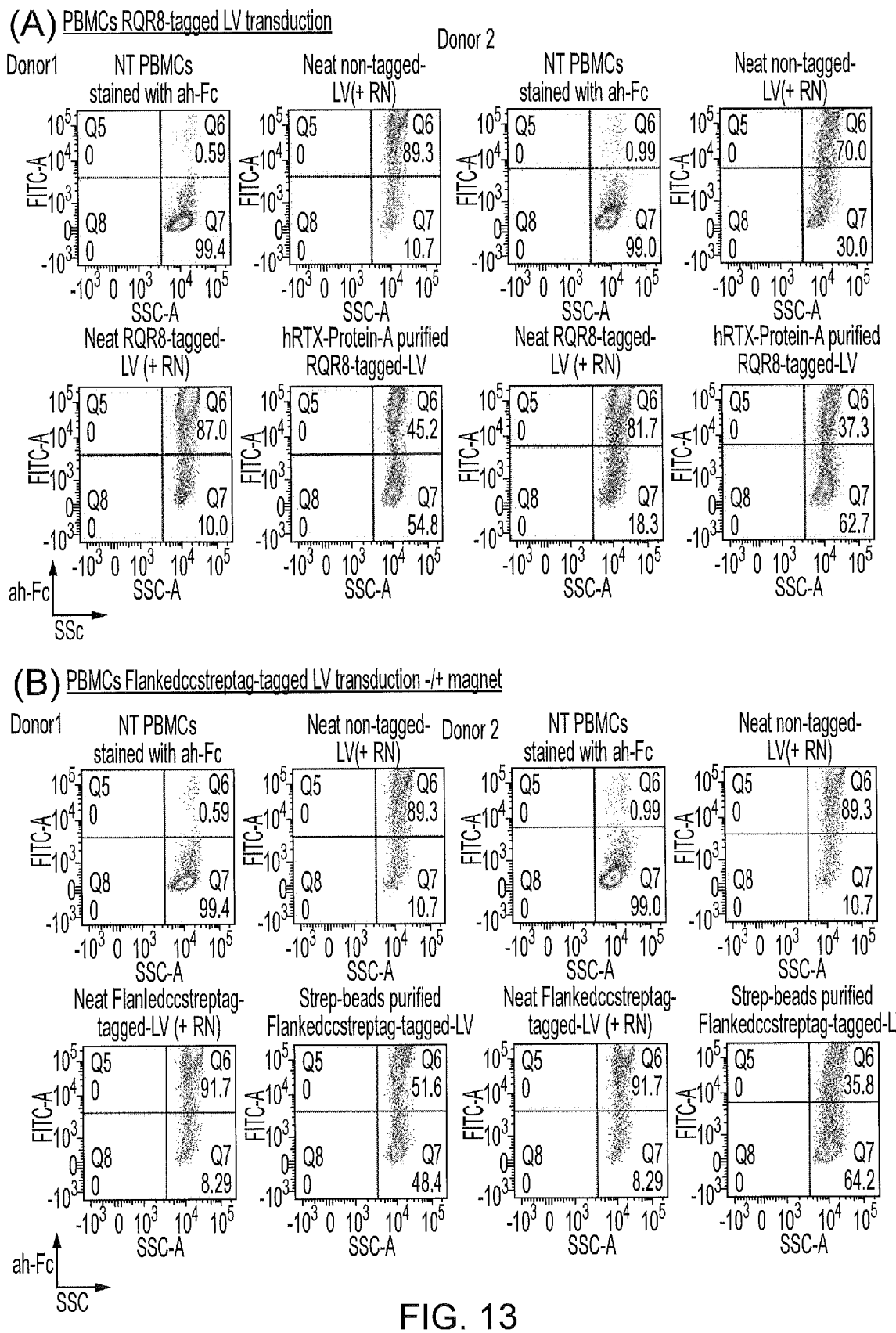

FIG. 13: PBMC transduction with Flankedccstreptag- and RQR8-tagged LV.

RDpro pseudotyped LV particles, encoding a chimeric antigen receptor (CAR) with an anti-human Fc spacer, were produced from 293T cells expressing the synthetic tags on their surface (RQR8 (A) and Flankedccstreptag (B)). Supernatant were treated exactly as in FIG. 10, separated into a crude fraction (Neat; which represent non-purified supernatant) and a purified fraction where flankedccstreptagl-tagged LV and RQR8-tagged LV were incubated with Streptavidin-Dynabeads and human Rituximab pre-incubated with Protein-A Dynabeads, respectively. PBMCs (n=2, 3 wells/condition) were transduced with neat RQR8 and Flankccstreptag-tagged-LV supernatant and non-tagged LV supernatant (control) using Retronectin coated plates. Whereas sorted LV particles of both tags were added onto PBMCs for transduction in the absence of rectronectin but with the absence or presence of a magnet under the plate for 1 hour at 37 C (n=3). Transduction efficiencies were determined by staining with anti-human-Fc antibody for the CAR, of the later conditions are plotted in the lower right panel with error bars representing standard deviation of n=3

FIG. 14: Sequences of engineered tagging proteins based on recombinant RD114 envelope proteins.

The Furin cleavage site is "RPKR" and is shown highlighted in bold italic. (a) To generate RD114 SU tagged at its amino terminus with RQR, the RQR8 sequence (highlighted in blue) was inserted just after the RD114 envelope signal peptide. To allow correct orientation for binding and to isolate from the envelope glycoprotein, a serine-glycine linker was inserted between RQR and SU (highlighted in gray). After processing, the RQR tag is at the extreme amino-terminus of the SU fragment. (b) To generate RD114 envelope TM tagged at its amino terminus with RQR, the tag was inserted just after the furin cleavage site. Again, a flexible linker was inserted between RQR and the TM fragment of RD114 envelope. After processing, RQR is accessible at the extreme amino-terminus of the TM domain. (c) To generate RD114 SU tagged at its amino terminus with flanked CC streptag, the tag sequence (highlighted in green) was inserted just after the RD114 envelope signal peptide. To allow correct orientation for binding and to isolate from the envelope glycoprotein, a serine-glycine linker was inserted between the tag and SU (highlighted in gray). After processing, the ccstreptag tag is at the extreme amino-terminus of the SU fragment. (d) To generate RD114 envelope TM tagged at its amino terminus with ccstreptag, the tag was inserted just after the furin cleavage site. Again, a flexible linker was inserted between the tag and the TM fragment of RD114 envelope. After processing, ccstreptag is accessible at the extreme amino-terminus of the TM domain.

Figure 15:
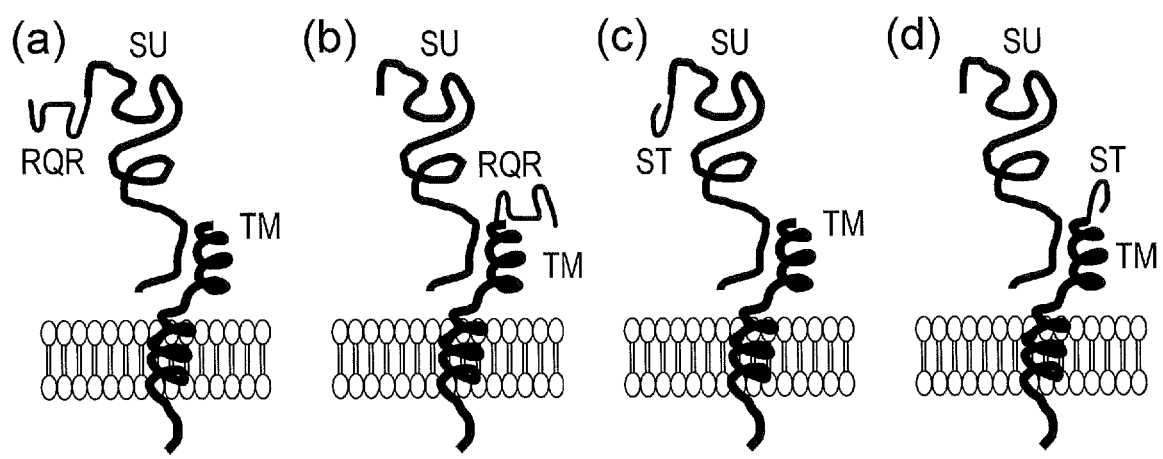

FIG. 15: Schematic diagram of the engineered tagging proteins based on recombinant RD114 envelope proteins.

The envelope glycoprotein is cleaved at a furin cleavage site to yield two fragments SU and TM which are connected via di-sulfide bonds. The tag (either RQR or a biotin mimic—ST are shown as examples), can be inserted either into the amino terminus of SU, just after the signal peptide or else at the amino-terminus of TM just after the furin cleavage site.

FIG. 16: RD-PRO and RD114-TR env protein sequence (transmembrane and endodomains highlighted)

Figure 17:
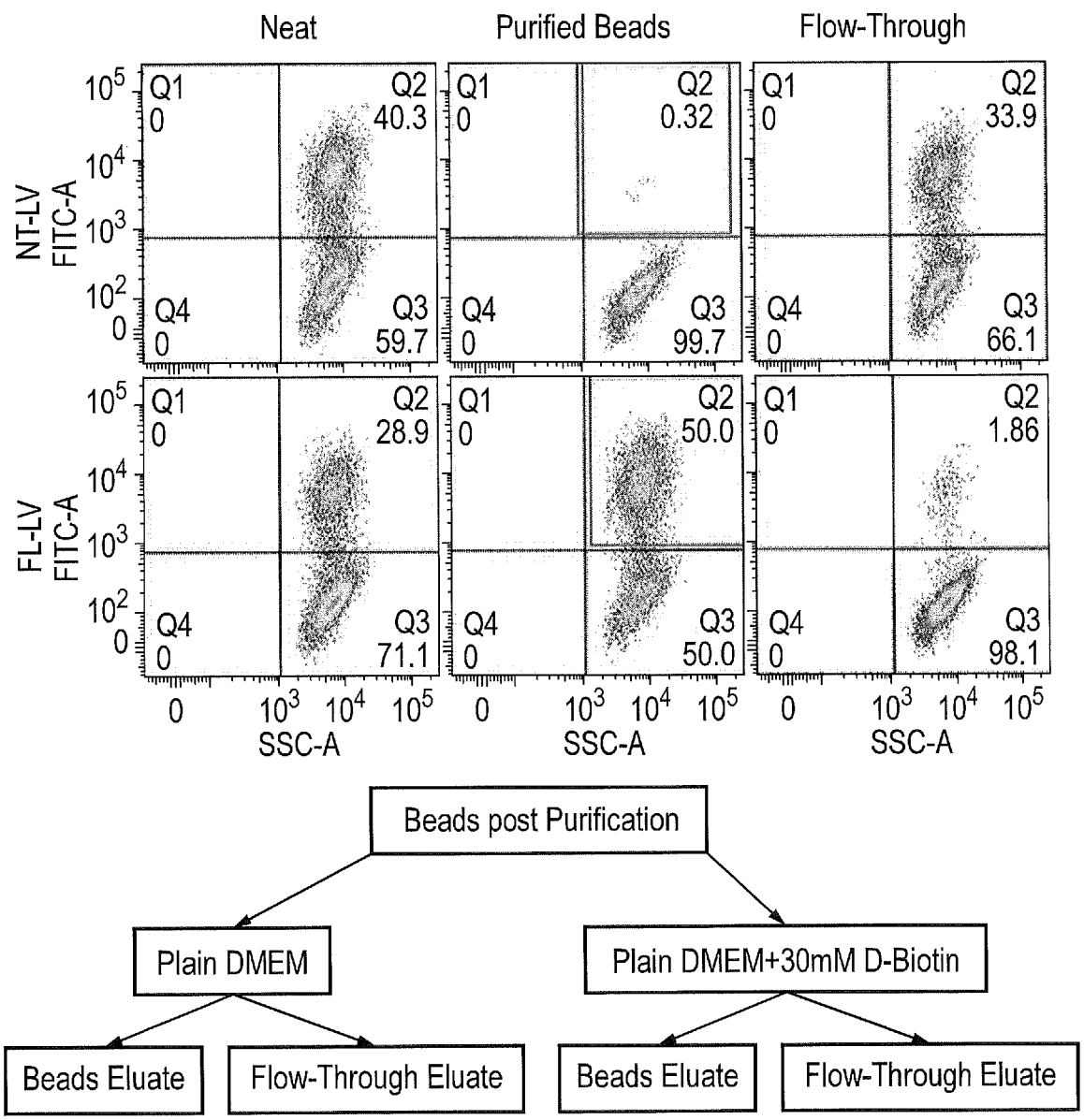

FIG. 17: Elution of tagged viral particles with Biotin

Flankedccstreptag-LV (FL-LV) and non-tagged LV (NT-LV) viral particles were purified using beads by magnetically separating the beads from cellular supernatant. LV-bound beads were then resuspended in either plain DMEM or DMEM with 30 mMD-Biotin. Flow cytometry was used to visualise tagged and untagged particles in the beads post-purification in the plain DMEM resuspension (NEAT) and, for the BMEM/Biotin resuspension, in the beads eluate (Purified Beads) and the flow-through eluate (Flow Through).

Figure 18:
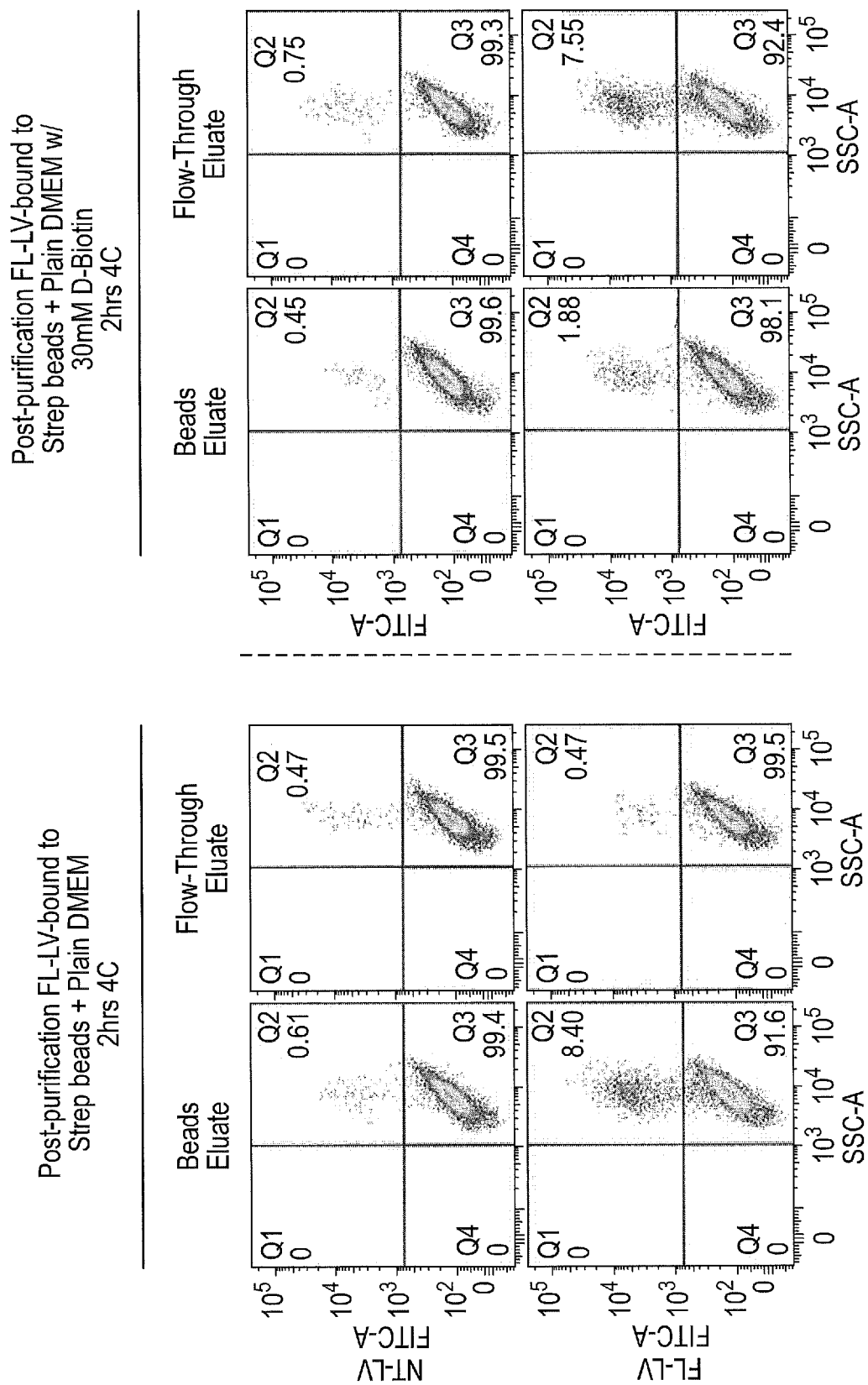

FIG. 18: Elution of tagged viral particles with Biotin

Flankedccstreptag-LV (FL-LV) and non-tagged LV (NT-LV) viral particles were purified using beads by magnetically separating the beads from cellular supernatant. LV-bound beads were then resuspended in either plain DMEM or DMEM with 30 mMD-Biotin. Flow cytometry was used to visualise tagged and untagged particles in the beads post-purification in the plain DMEM resuspension beads eluate and flow-through eluate (left hand side) the BMEM/Biotin resuspension beads eluate and the flow-through eluate (right hand side).

SUMMARY OF ASPECTS OF THE INVENTION

The present inventors have developed a system in which viral vector particles may be tagged indirectly by using a producer cell which expresses the tag at the cell surface. Since the tagging protein is expressed on the producer cell, the reading frame of the viral envelope is unaffected, which therefore preserves functional integrity and viral titre.

In a first aspect the present invention relates to a producer cell which expresses a tagging protein at the cell surface, such that retroviral vectors produced by the cell are tagged with the tagging protein. The tagging protein comprises:
  i) a binding domain which binds to a capture moiety
  ii) a spacer; and
  iii) a membrane targeting domain such that, when incorporated a retroviral vector, the tagging protein facilitates purification of the retroviral vector from cellular supernatant via binding of the tagging protein to the capture moiety.

The membrane targeting domain may comprise a transmembrane domain and an endodomain. The membrane targeting domain may comprise a GPI anchor.

The spacer may comprise a CD8 stalk or an equivalent thereof.

The tagging protein may also comprise a cleavage site, cleavage at which releases retroviral vectors bound to the capture moiety.

The tagging protein may comprise a linker between the binding domain and the spacer, which linker is or comprises the cleavage site. The cleavage site may be cleaved by thrombin.

Where the membrane targeting domain comprises a transmembrane domain and an endodomain; the transmembrane domain and endodomain may be effectively the same as the transmembrane and endodomain of the envelope protein of a retroviral vector.

The transmembrane domain and endodomain may be derived from the RD-PRO envelope protein.

The binding domain may comprise one or more streptavidin-binding epitope(s). The streptavidin-binding epitope may be a biotin mimicking peptide. Such a biotin mimic may bind streptavidin with a lower affinity than biotin, so that biotin may be used to elute streptavidin-captured retroviral vectors produced by the packaging cell.

The biotin mimic may be selected from the following group: Streptag (SEQ ID NO: 38) (described by Schmidt et al, Protein Eng. 1993 January; 6(1):109-22.), or streptag II (SEQ ID NO: 1) (described by Skerra et al, J. Mol. Biol. 255, 753-766 (1996)), nanotag in either short (SEQ ID NO: 35) or long formats (SEQ ID NO: 36) as described by Lamlar et al, Protein Expr. Purif. 33, 39-47 (2004)), SBP tag (SEQ ID NO: 37) as described by Keefe et a/(Protein Expr. Purif. 23, 440-446 (2001)), or the disulphide constrained tags described by Giebel et al (Biochemistry (Mosc.) 34, 15430-15435 (1995)) (henceforth termed flankedccstretag (SEQ ID NO: 2) and ccstreptag (SEQ ID NO: 3).)

The tagging protein may comprise two or more streptavidin-binding epitopes.

The tagging protein may comprise one or more of the amino acid sequence(s) shown as SEQ ID No. 1 to 5.

The binding domain may comprise glutathione s transferase.

The tagging protein may comprise the amino acid sequence shown as SEQ ID NO: 6.

The binding domain may comprise a rituximab-binding epitope and/or a Qbend10 epitope.

The binding domain may comprise RQR8.

The tagging protein may comprise the amino acid sequence shown as SEQ ID NO: 21.

The producer cell may be a packaging cell which comprises genes encoding retroviral Gag, Pol and Env proteins stably integrated within the cell genome.

In a second aspect the present invention provides a retroviral vector which comprises a producer cell-derived tagging protein as defined in relation to the first aspect of the invention.

In a third aspect the present invention provides a method for making a producer cell or a packaging cell according to the first aspect of the invention which comprises the step of introducing a nucleic acid which encodes a tagging protein as defined in relation to the first aspect of the invention into a cell, such that the tagging protein is expressed at the cell surface.

In an fourth aspect the present invention relates to a kit for making a producer cell according to the first aspect of the invention which produces retroviral vectors, the kitcomprising: a nucleic acid which encodes a tagging protein as defined in relation to the first aspect of the invention; and a retroviral vector genome; and optionally nucleic acids comprising retroviral gag, pol and env genes.

In a fifth aspect the present invention relates to a method for purifying a retroviral vector according to the second aspect of the invention which comprises the step of capture of the retroviral vector using the capture moiety.

The capture moiety may be immobilised on a solid substrate. The capture moiety may present in a binding matrix containing column, or immobilised on beads In a sixth aspect the present invention relates to a method for purifying a retroviral vector comprising a tagging protein which comprises a binding domain comprising a streptavidin-binding epitope which comprises the step of streptavidin capture of the retroviral vector.

The method may also comprise the step of eluting the streptavidin-captured retroviral vector with biotin or desthiobiotin.

In a seventh aspect the present invention relates to a method for purifying a retroviral vector comprising a tagging protein comprising a binding domain which comprises glutathione S transferase which comprises the step of capture of the retroviral vector using reduced glutathione.

In an eighth aspect the present invention relates to a method for purifying a retroviral vector comprises a tagging protein which comprises a binding domain comprises a rituximab and/or a QBend10 epitope which comprises the step of capture of the retroviral vector using a rituximab monoclonal antibody.

The method may further comprise the step of binding rituximab-captured retroviral vectors to Protein A.

DETAILED DESCRIPTION

In a first aspect the present invention provides a tagging protein comprising a binding domain which binds to a capture moiety; a spacer; and a membrane targeting domain.

The term "having" as used herein is synonymous with the term "comprising".

Binding Domain

'Binding domain' refers to an entity, for example an epitope, which is capable recognising and specifically binding to a target entity, for example a capture moiety.

The binding domain may comprise one or more epitopes which are capable of specifically binding to a capture moiety. For example the binding domains may comprise at least one, two, three, four or five epitopes capable of specifically binding to a capture moiety. Where the binding domain comprises more than one epitope, each epitope may be separated by a linker sequence, as described herein.

The binding domain may be releasable from the capture moiety upon the addition of an entity which has a higher binding affinity for the capture moiety compared to the binding domain.

Streptavidin-Binding Epitope

The binding domain may comprise one or more streptavidin-binding epitope(s). For example, the binding domain may comprise at least one, two, three, four or five streptavidin-binding epitopes.

Streptavidin is a 52.8 kDa protein purified from the bacterium *Streptomyces avidinii*. Streptavidin homo-tetramers have a very high affinity for biotin (vitamin B7 or vitamin H), with a dissociation constant $(Kd) \sim 10^{-15}$ M. Streptavidin is well known in the art and is used extensively in molecular biology and bionanotechnology due to the streptavidin-biotin complex's resistance to organic solvents, denaturants, proteolytic enzymes, and extremes of temperature and pH. The strong streptavidin-biotin bond can be used to attach various biomolecules to one another or on to a solid support. Harsh conditions are needed to break the streptavidin-biotin interaction, however, which may denature a protein of interest being purified.

The binding domain may be, for example, a biotin mimic. A 'biotin mimic' may refer to an short peptide sequence (for example 6 to 20, 6 to 18, 8 to 18 or 8 to 15 amino acids) which specifically binds to streptavidin.

As described above, the affinity of the biotin/streptavidin interaction is very high. It is therefore an advantage of the present invention that the binding domain may comprise a biotin mimic which has a lower affinity for streptavidin compared to biotin itself.

In particular, the biotin mimic may bind streptavidin with a lower binding affinity than biotin, so that biotin may be used to elute streptavidin-captured retroviral vectors. For example, the biotin mimic may bind streptavidin with a Kd of 1 nM to 100 uM.

The biotin mimic may comprise a sequence as shown in Table 1.

TABLE 1

Biotin mimicking peptides.

| name | Sequence | affinity |
| --- | --- | --- |
| Long nanotag | DVEAWLDERVPLVET (SEQ ID NO: 35) | 3.6nM |
| Short nanotag | DVEAWLGAR (SEQ ID NO: 36) | 17 nM |
| Streptag | WRHPQFGG (SEQ ID NO: 38) | |
| streptagII | WSHPQFEK (SEQ ID NO: 1) | 72 uM |
| SBP-tag | MDEKTTGWRGGHVVEGLAGELEQLRARLEHHPQGQREP (SEQ ID NO: 37) | 2.5 nM |
| ccstreptag | CHPQGPPC (SEQ ID NO: 3) | 230 nM |
| flankedccstreptag | AECHPQGPPCIEGRK (SEQ ID NO: 2) | |

The biotin mimic may be selected from the following group: StreptagII, Flankedccstreptag and ccstreptag.

The binding domain may comprise more than one biotin mimic. For example the binding domain may comprise at least one, two, three, four or five biotin mimics.

Where the binding domain comprises more than one biotin mimic, each mimic may be the same or a different mimic. For example, the binding domain may comprise two StreptagII biotin mimics separated by a linker (for example as shown by SEQ ID NO: 4) or two Flankedccstreptag separated by a linker (for example as shown by SEQ ID NO: 5).

```
(StreptagII-d8-x2)
                                          SEQ ID NO: 4
WSHPQFEKSGGGGSPAPRPPTPAPTIASWSHPQFEK (Flankedccstreptag-d8-x2)
                                          SEQ ID NO: 5
ECHPQGPPCIEGRKSSGGGGSPAPRPPTPAPTIASECHPQGPPCIEGRKS
```

Glutathione S-Transferase

The binding domain may comprise a glutathione S-transferase (GST) domain.

GSTs comprise a family of eukaryotic and prokaryotic phase II metabolic isozymes which catalyze the conjugation of the reduced form of glutathione (GSH) to xenobiotic substrates for the purpose of detoxification. The GST family consists of three superfamilies: the cytosolic, mitochondrial, and microsomal (also known as MAPEG) proteins (Udomsinpraser et al. Biochem. J. (2005) 388 (Pt 3): 763-71).

The GST protein has a strong binding affinity for GSH and this interaction is commonly used in molecular biology to enable the isolation of a GST-tagged protein from a protein mixture.

An amino acid sequence for GST is shown as SEQ ID NO: 6.

```
(GST)
                                          SEQ ID NO: 6
MGTSLLCWMALCLLGADHADAMSPILGYWKIKGLVQPTRLLLEYLEEKY
EEHLYERDEGDKWRNKKFELGLEFPNLPYYIDGDVKLTQSMAIIRYIAD
KHNMLGGCPKERAEISMLEGAVLDIRYGVSRIAYSKDFETLKVDFLSKL
PEMLKMFEDRLCHKTYLNGDHVTHPDFMLYDALDVVLYMDPMCLDAFPK
LVCFKKRIEAIPQIDKYLKSSKYIAWPLQGWQATFGGGDHPPKSDLEVL
FQGPLG
```

Rituximab-Binding Epitope

The present tagging protein may comprise a binding domain which comprises a rituximab-binding epitope (R epitope) and/or a Qbend10 epitope (Q epitope).

A rituximab-binding epitope refers to an epitope which specifically binds rituximab. For example, the rituximab-binding epitope may be based on the CD20 B-cell antigen.

The Rituximab-binding epitope sequence from CD20 is CEPANPSEKNSPSTQYC (SEQ ID No. 7)

Perosa et al (2007, J. Immunol 179:7967-7974) describe a series of cysteine-constrained 7-mer cyclic peptides, which bear the antigenic motif recognised by the anti-CD20 mAb Rituximab but have different motif-surrounding amino acids. Eleven peptides were described in all, as shown in the following table:

| Peptide | Insert sequence |
| --- | --- |
| R15-C | acPYANPSLc (SEQ ID No. 8) |
| R3-C | acPYSNPSLc (SEQ ID No. 9) |
| R7-C | acPFANPSTc (SEQ ID No. 10) |
| R8-, R12-, R18-C | acNFSNPSLc (SEQ ID No. 11) |
| R14-C | acPFSNPSMc (SEQ ID No. 12) |
| R16-C | acSWANPSQc (SEQ ID No. 13) |
| R17-C | acMFSNPSLc (SEQ ID No. 14) |
| R19-C | acPFANPSMc (SEQ ID No. 15) |

-continued

| Peptide | Insert sequence |
|---|---|
| R2-C | acWASNPSLc (SEQ ID No. 16) |
| R10-C | acEHSNPSLc (SEQ ID No. 17) |
| R13-C | acWAANPSMc (SEQ ID No. 18) |

Li et al (2006 Cell Immunol 239:136-43) also describe mimetopes of Rituximab, including the sequence:

```
                                          (SEQ ID No. 19)
QDKLTQWPIKINLE.
```

The polypeptide of the present invention comprises a Rituximab-binding epitope having an amino acid sequence selected from the group consisting of SEQ ID No. 7-19 or a variant thereof which retains Rituximab-binding activity.

QBend10

The CliniMACS CD34 selection system utilises the QBEnd10 monoclonal antibody to achieve cellular selection. The present inventors have previously mapped the QBEnd10-binding epitope from within the CD34 antigen (see WO 2013/153391) and determined it to have the amino acid sequence shown as SEQ ID No. 20.

(SEQ ID No. 20)
ELPTQGTFSNVSTNVS.

The binding domain of the present tagging protein the present invention may comprise a QBEnd10-binding epitope having the amino acid sequence shown as SEQ ID No. 20 or a variant thereof which retains QBEnd10-binding activity.

RQR8

The present tagging protein may comprise a binding domain which comprises or consists of 136 amino acid sequence shown as SEQ ID NO: 21.

(RQR8)
SEQ ID NO: 21
CPYSNPSLCSGGGGSELPTQGTFSNVSTNVSPAKPTTTACPYSNPSLCSG
GGGSPAPRPPTPAPTIASQPLSLRPEACRPAAGGAVHTRGLDFACDIYIW
APLAGTCGVLLLSLVITLYCNHRNRRRVCKCPRPVV

Variant

The present tagging protein may comprise a variant of a binding domain as described herein. For example, the binding domain may be based on a sequence provided herein but comprises one or more amino acid mutations, such as amino acid insertions, substitutions or deletions, provided that the epitope retains binding activity of the entity or epitope on which it is based. In particular, the sequence may be truncated at one or both terminal ends by, for example, one or two amino acids.

Deliberate amino acid substitutions may be made on the basis of similarity in polarity, charge, solubility, hydrophobicity, hydrophilicity, and/or the amphipathic nature of the residues as long as binding activity of the epitope is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

| | | |
|---|---|---|
| Conservative substitutions may be made, for example according to the Table below. Amino acids in the same block in the second column and in the same line in the third column may be substituted for each other:ALIPHATIC | Non-polar | G A P |
| | | I L V |
| | Polar-uncharged | C S T M<br>N Q |
| | Polar-charged | D E<br>K R |
| AROMATIC | | H F W Y |

The binding domain may, for example, contain 5 or fewer, 4 or fewer, 3 or fewer, 2 or fewer or 1 amino acid mutation(s) compared to a binding domain sequence as shown herein.

The binding domain may consist essentially of a binding domain sequence as shown herein or a variant thereof which retains the binding activity of the binding domain on which it is based. The binding domain may consist of a binding domain sequence as shown herein or a variant thereof which retains that binding activity of the binding domain on which it is based.

Spacer

The tagging protein of the present invention comprises a spacer sequence to connect the binding domain and the transmembrane domain and spatially separate the two domains.

The spacer sequence may, for example, comprise a CD8 stalk or a Glycosylphosphatidylinositol (GPI) anchor. The spacer may comprise an equivalent of a CD8 stalk or a GP1 anchor—i.e. a sequence which provides the function of spatially separating the binding domain and the transmembrane domain. For example the linker may comprise an alternative linker sequence which has similar length and/or domain spacing properties as a CD8 stalk or a GPI anchor.

The spacer may be a short spacer, for example a spacer which comprises less than 100, less than 80, less than 60 or less than 45 amino acids. The spacer may be or comprise a CD8 stalk or may comprise a GPI anchor—; the synthesis and attachment of which to the protein is directed by a GPI signal sequence, or a modified version thereof.

Examples of amino acid sequences for these linkers or GPI signal sequences are given below:

(CD8 stalk)
SEQ ID NO: 22
PAPRPPTPAPTIASQPLSLRPEACRPAAGGAVHTRGLDFACDIYIWAPLA
GTCGVLLLSLVITLYCNHRNRRRVCKCPR (CD8 stalk + Linker)
SEQ ID NO: 23
SGGGGSPAPRPPTPAPTIASQPLSLRPEACRPAAGGAVHTRGLDFACDIY
IWAPLAGTCGVLLLSLVITLYCNHRNRRRVCKCPR (GPI signal sequence)
SEQ ID NO: 24
ASSNISGGIFLFFVANAIIHLFCFS The spacer may also comprise one or more linker motifs to introduce a chain-break. A chain-break separates two distinct domains but allows orientation in different angles. Such sequences include the sequence SDP, and the sequence SGGGSDP (SEQ ID No. 25).

The linker may comprise a serine-glycine linker, such as SGGGGS (SEQ ID No. 26).

Membrane Targeting Domain

The tagging protein of the present invention comprises a membrane targeting domain.

A 'membrane targeting domain' is an entity which preferentially localises to the membrane and therefore anchors the present tagging protein to the membrane of, for example, a packaging cell or a retroviral vector.

The membrane targeting domain may be a transmembrane domain and an endodomain.

A transmembrane domain is a hydrophobic alpha helix which spans a cell membrane and typically found in transmembrane proteins.

Where the tagging protein has a transmembrane domain, it also comprises an endodomain, which orientates to the interior of, for example, the packaging cell or retroviral vector.

The endodomain comprises polar residues which anchor the tagging protein to the I membrane.

The endodomain may directly enhance incorporation into the virion. Retroviral glycoprotein endodomains contain motifs which enhance incorporation into the virion. In case of a lentiviral vector for instance, the tagging protein may comprise an endodomain engineered to enhance incorporation into a lenvirus, for instance akin to that of RD-PRO (see Ikeda et al.; Nat Biotechnol. 2003 May; 21(5):569-72) or RD114-TR (Sandin et al; 2002; Blood: Volume 100; Issue 3; Pages 823-32). An RD-PRO and RD114-TR env protein sequence is shown in FIG. 16.

For example the tagging protein may comprise the transmembrane domain and endodomain shown as SEQ ID NO: 27

(RD-PRO TM and endodomain)
SEQ ID NO: 27
YLLPLLGPLLTLLULTIGPCVFSRLMAFINDRLNVSQNYPIVQQYQALKA
EEEAQD The membrane targeting domain may be a GPI anchor.

GPI anchoring is a post-translational modification which occurs in the endoplasmic reticulum. Preassembled GPI anchor precursors are transferred to proteins bearing a C-terminal GPI signal sequence (see Kinoshita et al.; J Biochem; 122, 251-257 (1997)). During processing, the GPI anchor replaces the GPI signal sequence and is linked to the target protein via an amide bond. The GPI anchor targets the mature protein to the membrane.

The present tagging protein may comprise a GPI signal sequence. For example the tagging protein may comprise a sequence shown as SEQ ID NO: 24.

The GPI anchor may provide the function of both the spacer domain and the membrane targeting domain of the present tagging protein. As such the spacer domain and the membrane targeting domain of the tagging protein may be a GPI anchor.

Cleavage Site

The tagging protein of the invention may comprise a cleavage site, cleavage at which releases retroviral vectors bound to the capture moiety.

A 'cleavage site' refers to an amino acid sequence or motif which is specifically recognised by an enzyme which is capable of breaking a peptide bond within, or proximal to, the cleavage site. As such, once the retroviral particle has been bound to the capture moiety, addition of the enzyme to the retroviral-capture moiety complex results in cleavage of the tagging protein at the cleavage site and release of the retroviral vector from the capture moiety.

The cleavage site may be present in a linker sequence between the binding domain and the spacer. The linker may be, or may comprise, the cleavage sequence.

The cleavage site may be cleaved by thrombin. Thrombin is produced in vivo by the enzymatic cleavage of two sites on prothrombin by activated Factor X. In the blood coagulation pathway, thrombin acts to convert factor XI to XIa, VIII to VIIIa, V to Va, fibrinogen to fibrin, and XIII to XIIIa.

The thrombin cleavage site may be, for example, LVPRGS (SEQ ID NO: 28), wherein thrombin selectively cleaves between the Arginine and Glycine residues.

Signal Peptide

The tagging protein of the invention may comprise a signal peptide to aid in its production.

The core of the signal peptide may contain a long stretch of hydrophobic amino acids that has a tendency to form a single alpha-helix. The signal peptide may begin with a short positively charged stretch of amino acids, which helps to enforce proper topology of the polypeptide during translocation. At the end of the signal peptide there is typically a stretch of amino acids that is recognized and cleaved by signal peptidase. Signal peptidase may cleave either during or after completion of translocation to generate a free signal peptide and a mature protein. The free signal peptides are then digested by specific proteases.

The signal peptide may be at the amino terminus of the molecule.

The signal peptide may comprise the SEQ ID No. 29 or 30 or a variant thereof having 5, 4, 3, 2 or 1 amino acid mutations (insertions, substitutions or additions) provided that the signal peptide still functions to cause secretion of the bi-specific molecule.

SEQ ID No. 29:
METDTLLLVVVLLLVVVPGSTG

SEQ ID No. 30:
MGTSLLCWMALCLLGADHADG

The signal peptides of SEQ ID No. 29 and 30 are compact and highly efficient. They are predicted to give about 95% cleavage after the terminal glycine, giving efficient removal by signal peptidase.

Retrovirus

The tagging protein of the present invention facilitates the purification of a retroviral vector from a cellular supernatant via binding of the tagging protein to a capture moiety.

The term 'purification' is used according to its conventional meaning to refer to the process of isolating the retroviral vector from a mixture, for example a cell culture supernatant, such that the retroviral vector is substantially free from contaminants The concept of using viral vectors for gene therapy is well known (Verma and Somia (1997) Nature 389:239-242).

There are many retroviruses. For the present application, the term "retrovirus" includes, but is not limited to: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758-763).

In a preferred embodiment, the retroviral vector is derivable from a lentivirus.

Lentiviruses also belong to the retrovirus family, but they can infect both dividing and non-dividing cells (Lewis et al (1992) EMBO J. 3053-3058).

The lentivirus group can be split into "primate" and "non-primate". Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

Details on the genomic structure of some lentiviruses may be found in the art. By way of example, details on HIV and EIAV may be found from the NCBI Genbank database (i.e. Genome Accession Nos. AF033819 and AF033820 respectively). Details of HIV variants may also be found at http://hiv-web.lanl.gov. Details of EIAV variants may be found through http://www.ncbi.nlm.nih.gov.

During the process of infection, on entry into the susceptible host cell, the lentiviral RNA genome is copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which, for a wild-type replication competent virus can leave the cell by a process sometimes called "budding".

Lentiviruses have three main genes coding for the viral proteins in the order: 5'-gag-pol-env-3'. There are two regulatory genes, tat and rev. There are additional accessory genes depending on the virus (e.g., for HIV-1: vif, vpr, vpu, nef) whose products are involved in regulation of synthesis and processing viral RNA and other replicative functions. The Long terminal repeat (LTR) is about 600 nt long, of which the U3 region is 450, the R sequence 100 and the U5 region some 70 nt long.

Viral proteins involved in early stages of replication include Reverse Transcriptase and Integrase. Reverse Transcriptase is the virally encoded RNA-dependent DNA polymerase. The enzyme uses the viral RNA genome as a template for the synthesis of a complementary DNA copy. Reverse transcriptase also has RNaseH activity for destruction of the RNA-template. Integrase binds both the viral cDNA generated by reverse transcriptase and the host DNA. Integrase processes the LTR before inserting the viral genome into the host DNA. Tat acts as a trans-activator during transcription to enhance initiation and elongation. The Rev responsive element acts post-transcriptionally, regulating mRNA splicing and transport to the cytoplasm.

The lentiviral proteome consists of five major structural proteins and 3-4 non-structural proteins (3 in the primate lentiviruses). Gp120 glycosylated surface envelope protein SU, encoded by the viral gene env, Gp41 glycosylated transmembrane envelope protein TM, also encoded by the viral gene env, P24 non-glycosylated capsid protein CA, encoded by the viral gene gag, P17 non-glycosylated matrix protein MA, also encoded by gag and non-glycosylated capsid protein NC, also encoded by gag.

The envelope proteins SU and TM are glycosylated in at least some lentiviruses (e.g. HIV, SIV). Glycosylation may play a structural role in the concealment and variation of antigenic sites necessary for the host to mount an immune system response. SU and TM form a complex that interacts specifically with cellular receptor proteins. This interaction leads ultimately to infection by fusion of the viral membrane with the cell membrane.

As used herein the term "lentiviral vector", when referring to a lentiviral vector system also includes a lentiviral vector particle capable of transducing a recipient cell with a nucleotide of interest (NOI).

A lentiviral vector particle includes the following components: a vector genome, which may contain one or more NOIs, a nucleocapsid encapsidating the nucleic acid, and a membrane surrounding the nucleocapsid.

The term "nucleocapsid" refers to at least the group specific viral core proteins (gag) and the viral polymerase (pol) of a retrovirus genome. These proteins encapsidate the packagable sequences and are themselves further surrounded by a membrane containing an envelope glycoprotein.

The term "vector genome" refers to both to the RNA construct present in the lentiviral vector particle and the integrated DNA construct. The term also embraces a separate or isolated DNA construct capable of encoding such an RNA genome. A lentiviral genome should comprise at least one component part derivable from a lentivirus. The term "derivable" is used in its normal sense as meaning a nucleotide sequence or a part thereof which need not necessarily be obtained from a virus such as a lentivirus but instead could be derived therefrom. By way of example, the sequence may be prepared synthetically or by use of recombinant DNA techniques.

Retroviral Envelope Protein

In a further aspect, the present invention provides a retroviral envelope protein which is, or comprises, a tagging protein according to the first aspect of the invention.

'Retroviral envelope protein' refers to the SU and/or TM proteins, as described above in relation to lentiviruses.

In one embodiment the retroviral envelope protein is a lentiviral envelope protein.

For example, a retroviral envelope protein of the present invention may be based on the RD114 SU or TM protein or the RDpro SU or TM protein. The term 'based on' indicates that the protein is derived or derivable from the respective envelope protein. The amino acid sequences of RD114 TM protein and its endodomain and the RDpro TM protein and its endodomain are shown in FIG. 16. The retroviral envelope protein expressed by the producer cell of the present invention may comprise one of these sequences or a variant which comprises 80, 90, 95 or 99% identity to one of the sequences shown in FIG. 16.

The retroviral envelope protein which is, or comprises, the tagging protein is able to function to encapsulate the nucleocapsid and thus form a retroviral particle.

The retroviral envelope protein may comprise a tagging protein at the N or C-terminus.

The retroviral envelope protein may comprise or consist of a sequence shown as one of SEQ ID NO: 31-34 in FIG. 14 or a variant thereof having 80, 90, 95 or 99% identity to one of the sequences shown in FIG. 14 which retains the function of the envelope protein to act as a tag.

Nucleic Acid Sequence

In a further aspect the present invention provides a nucleic acid sequence which encodes a tagging protein or envelope protein of the present invention.

The nucleic acid sequence may be an RNA or DNA sequence or a variant thereof.

The present invention also provides a vector which comprises such a nucleic acid sequence.

Vector

The present invention further provides a retroviral vector which comprises a tagging protein or an envelope protein according to the present invention.

Producer Cell and Packaging Cell

As used herein, the term "producer cell" refers to a cell which contains all the elements necessary for production of retroviral vector particles.

As used herein, the term "packaging cell" refers to a cell which contains those elements necessary for production of infectious recombinant virus which are lacking in the RNA genome. Typically, such packaging cells contain one or more producer plasmids which are capable of expressing viral structural proteins (such as gag-pol and env, which may be codon optimised) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

Packaging cell lines may be readily prepared (see also WO 92/05266), and utilised to create producer cell lines for the production of retroviral vector particles.

Producer cells/packaging cells can be of any suitable cell type. Producer cells are generally mammalian cells but can be, for example, insect cells.

By using producer/packaging cell lines, it is possible to propagate and isolate quantities of retroviral vector particles (e.g. to prepare suitable titres of the retroviral vector particles) for subsequent transduction of a site of interest.

The packaging cell lines are useful for providing the gene products necessary to encapsidate and provide a membrane protein for a high titre vector particle production. The packaging cell may be a cell cultured in vitro such as a tissue culture cell line. Suitable cell lines include but are not limited to mammalian cells such as murine fibroblast derived cell lines or human cell lines. The packaging cell line may be a human cell line, such as for example: HEK293, 293-T, TE671, HT1080.

There are two common procedures for generating producer cells. In one, the sequences encoding retroviral Gag, Pol and Env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region.

However, when a vector genome (having a psi region) is introduced into the packaging cell line, the helper proteins can package the psi-positive recombinant vector RNA to produce the recombinant virus stock. This can be used to transduce recipient cells. The recombinant virus whose genome lacks all genes required to make viral proteins can infect only once and cannot propagate. Hence, a nucleic acid sequence can be introduced into a host cell genome without the generation of potentially harmful retrovirus.

The second approach is to introduce the three different DNA sequences that are required to produce a retroviral vector particle (i.e. the env coding sequences, the gag-pol coding sequence and the defective retroviral genome containing one or more NOIs) into the cell at the same time by transient transfection and the procedure is referred to as transient triple transfection. WO 94/29438 describes the production of producer cells in vitro using this multiple DNA transient transfection method. WO 97/27310 describes a set of DNA sequences for creating retroviral producer cells either in vivo or in vitro for re-implantation.

The components of the viral system which are required to complement the vector genome may be present on one or more "producer plasmids" for transfecting into cells.

The present invention provides a producer cell which expresses a tagging protein according to the first aspect of the invention at the cell surface, such that retroviral vectors produced by the cell are tagged with the tagging protein.

The producer cell of the present invention may be a packaging cell which comprises genes encoding retroviral Gag, Pol and Env proteins stably integrated within the genome. The packaging cell line may be transduced with a viral vector system comprising the genome or transfected with a plasmid carrying a DNA construct capable of encoding the RNA genome.

The packing cell may comprise an Env protein which is an envelope protein of the present invention. Specifically, the Env protein may be an envelope protein which is or comprises a tagging protein according to the first aspect of the invention.

The tagging protein may be expressed in the producer cell or packaging cell of the present invention using techniques which are well known in the art. For example the producer cell line may be transduced with a viral vector system or a DNA construct comprising a nucleic acid sequence which is capable of encoding a tagging protein according to the first aspect of the invention.

As such the present invention further relates to a method for making a producer cell or a packaging cell according to the present invention which comprises the step of introducing a nucleic acid which encodes a tagging protein according to the first aspect of the invention into a cell, such that the tagging protein is expressed at the cell surface.

The present invention also provides a kit for making a producer cell of the invention, comprising:
 (i) a nucleic acid which encodes a tagging protein according to the first aspect of the invention;
 (ii) a retroviral vector genome; and optionally
 (iii) nucleic acids comprising retroviral gag, pol and env genes.

The present invention further relates to producer cells which produce retroviral vectors which comprise an envelope protein of the present invention. Specifically, the producer cells may produce retroviral vectors which comprise an envelope protein which is or comprises a tagging protein according to the first aspect of the invention.

The present invention also provides a kit for making such a producer cell which comprises:
 (i) a nucleic acid which encodes a retroviral Env protein of the present invention; and
 (ii) nucleic acid(s) encoding retroviral Gag and Pol proteins; and optionally
 (iii) a retroviral vector genome.

The retroviral vector genome may be incapable of encoding the proteins gag, pol and env. The kit may thus comprise one or more producer plasmids encoding env, gag and pol, for example, one producer plasmid encoding env and one encoding gag-pol.

Where the retrovirus vector is a lentiviral vector, a packaging cell, producer cell or kit as described above may also comprise a Rev gene or a nucleic acid comprising a Rev gene.

Method

In a further aspect the present invention provides a method for purifying a retroviral vector comprising a tagging protein according to the first aspect of the invention; which comprises the step of capture of the retroviral vector using the capture moiety.

It is envisaged that the use of a plurality of tagging proteins which comprise one of a transmembrane domain, a GPI anchor or a retroviral envelope protein transmembrane domain will increase the efficiency of retrovirus vector capture.

The capture moiety may be immobilised on a solid state or substrate. For example, the capture moiety may be present in a binding matrix containing column or immobilised on beads.

The method may be performed using a tagging protein according to the first aspect of the invention wherein the binding domain comprises a streptavidin-binding epitope. Herein, the method may comprise the step of streptavidin capture of the retroviral vector. The method may also comprise the step of eluting the streptavidin-captured retroviral vector with biotin.

The method may be performed using a tagging protein according to the first aspect of the invention wherein the binding domain comprises GST. Herein the method may comprise the step of capture of the retroviral vector using reduced glutathione (GSH).

The method may be performed using a tagging protein according to the first aspect of the invention wherein the binding domain comprises a rituximab-binding epitope and/or a Qbend10 epitope. The method may be performed using a tagging protein according to the first aspect of the invention wherein the binding domain comprises a R8RQ. Herein, the method may comprise the step of capture of the retroviral vector using a rituximab monoclonal antibody. The method may further comprise the step of binding the rituximab-captured retroviral vector to Protein A.

The invention will now be further described by way of Examples, which are meant to serve to assist one of ordinary skill in the art in carrying out the invention and are not intended in any way to limit the scope of the invention.

EXAMPLES

Example 1—Selecting a Biotin-Mimic Epitope

Figure 1:
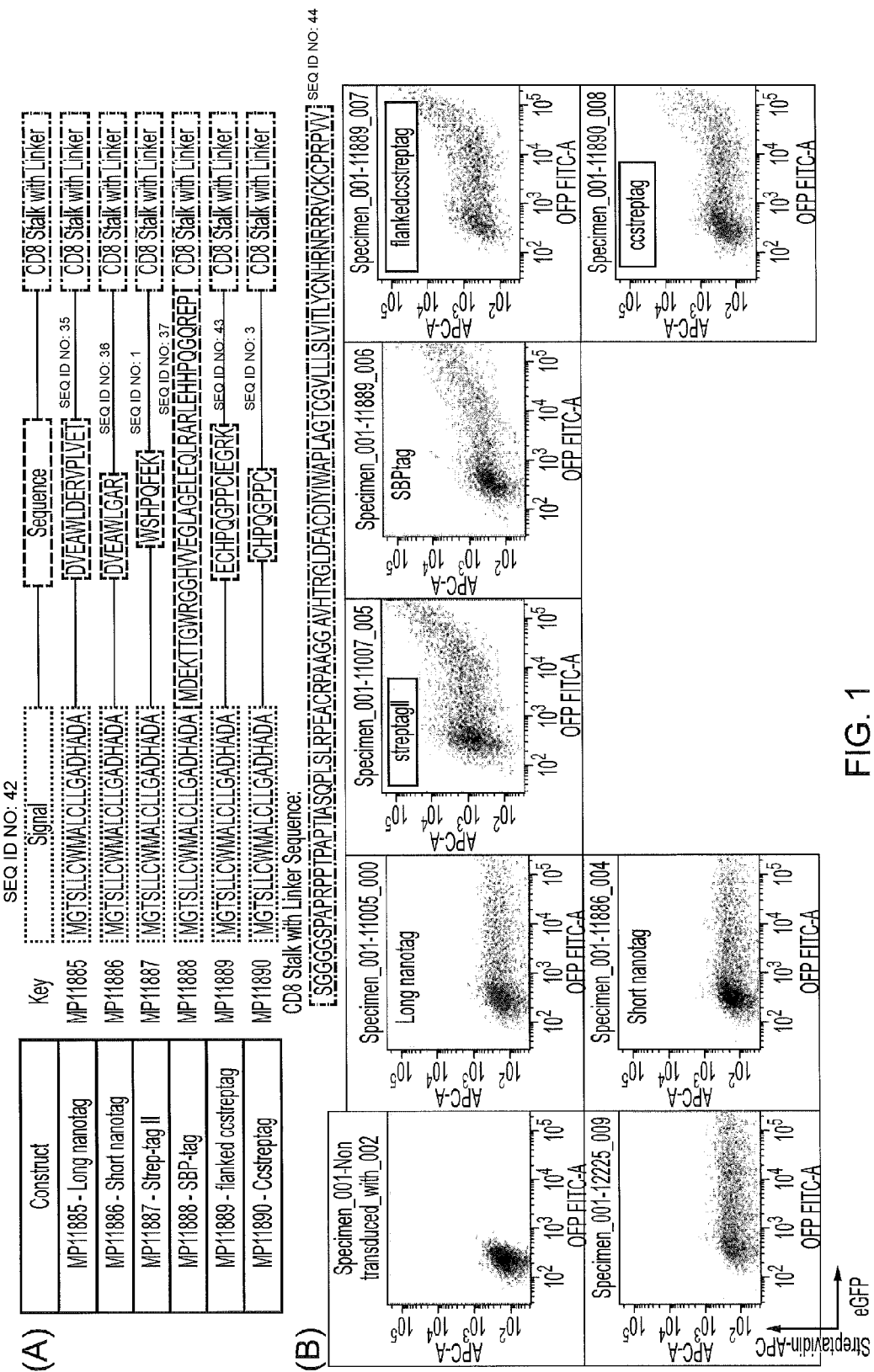
FIG. 1: Testing the binding of a Streptavidin-binding epitope.

Six biotin mimicking peptide tags were selected to study how well they might bind streptavidin when expressed as part of a cell surface protein (FIG. 1A). An expression construct coding for a signal peptide attached to the amino terminal of theses tags was generated. In addition, the carboxy terminal of these peptide tags was attached to the CD8 stalk, CD8 transmembrane domain and a short part of the CD8 endodomain sufficient to anchor the protein to the membrane. To test their binding to streptavidin, HEK 293T cells were transfected with each construct individually and 48 hrs post-transfection cells were harvested and stained with Streptavidin conjugated to the fluorophore Allophycocyanin (APC) (FIG. 1B). Three tags, long nanotag, short nanotag and SBPtag did not exhibit any binding to streptavidin in this format; whereas StreptagII, Flankedccstretag and ccstreptag successfully bound to Streptavidin compared to the negative control.

The optimal format to express these tags on the cell surface for streptavidin binding was then investigated. Additional plasmids were constructed where these tags are expressed on a GPI anchor with one copy of the tags' open reading frames and GPI anchor with two copies of the open reading frames separated by a CD8-based linker (the annotated amino acid sequences of these constructs are depicted in FIG. 2). The binding of these tags was compared with that of the original constructs where the epitopes were placed on a CD8 stalk.

To test their binding to Streptavidin, HEK 293T cells were transiently transfected with the constructs and stained 48 hrs post-transfection with Streptavidin-APC (FIG. 3). Positive control cells expressed a QBEND/10 antibody binding tag (Q8); here staining with biotinylated QBEND/10 allowed us to compare wild-type biotin binding of Streptavidin target with that of the biotin mimicking tags as a control.

All three tags expressed on a GPI anchor with one open reading frame (x1) did not bind Streptavidin-APC as their staining have the same profile as the negative control. Tags expressed on a CD8 stalk or a GPI anchor with two open reading frames (2x) successfully bound to streptavidin as indicated by the positive cells for the APC channel. The three tags had no significant difference in binding when expressed on CD8 stalk. Conversely, Flankedccstreptag showed a higher binding efficiency than StreptagII and ccstreptag on a GPI (x2).

The capacity of these tags to sort lentivirus with streptavidin-beads using both Flankedccstreptag-CD8stalk (MP11889, FIG. 2) and Flankedccstreptag-d8-x2-GPI (MP13024, FIG. 2) was then investigated.

Example 2—Sorting K562 Cells Expressing a Biotin-Mimic Epitope

To establish that the two versions of Flankedccstreptag are able to purify lentivirus from cellular supernatant, an initial experiment was carried out involving sorting of K562 cells expressing these tags on their surface using streptavidin beads. We reasoned that if the tags could attach to a streptavidin matrix while expressed on cells with sufficient stability to allow sorting of expressing cells, they should be suitable for lentiviral capture too.

K562 cells were retrovirally transduced to express the two tags and transduction efficiencies were determined by eGFP expression using flow cytometry (FIG. 4 Transduced K562 plot). Subsequently, transduced cells were mixed with non-transduced K562 to assess the efficiency of sorting using two streptavidin-beads sourced from Life technologies (Dynabeads) and Miltenyi (Microbeads). Sorting was performed as per manufacturer protocol. Sorted cell fractions were collected for both sorting for each epitope tag as well as their respective flow-through. K562 cells expressing both flankedccstreptag-d8-x2-GPI and flankedccstreptag-L8 were successfully sorted from the mixture with NT K562 population using streptavidin-dynabeads as indicated by the lack of eGFP positive cells in the flow-through fractions and their presence in the sorted fractions. Sorting with streptavidin microbeads from Miltenyi was successful. Additionally, it was found that flankedccstreptag on a CD8 stalk exhibited a higher binding efficiency to the streptavidin-APC antibody stain compared to flankedccstreptag-d8-x2-GPI.

Example 3—Indirect Tagging of Lentiviral Particles with Biotin-Mimic Epitopes It was then investigated whether expression of the tags in HEK293T cells resulted in viral particles which bud out of the cell to mature acquiring the epitopes on their surface.

293T cells expressing both epitopes separately were established by retroviral transduction (FIG. 5). Transduction efficiencies of the cells were almost 100% positive cells based on eGFP expression. Subsequently, these cells along with NT-293T cells (control) were triple transfected to produced VSV-G-pseudotyped lentivirus using a second generation packaging system. Supernatants were harvested 48 hrs post-transfection and processed to remove any suspended 293T cells. Subsequently, supernatants were incubated with streptavidin-dynabeads for 2 hrs at 4° C. with rotation. Beads were then magnetically purified and resuspended in fresh media. Successively, sorted beads were added onto NT-293T cells which were stained for transgene expression 72 hrs-post-transduction (FIG. 6).

All three supernatants produced functional lentiviral particles, as indicated by the high transduction efficiency seen in all three crude supernatants by transgene staining on target 293T cells (FIG. 6A).

The transduction efficiencies of beads-purified fraction from both LV-MP14585 (23.7% and 14.2%) and LV-MP14586 (11.1% and 6.45%) are higher than that of LV-NT (1.43% and 2.22%). This shows that viral particles not only acquired the epitopes on their surface but also that both streptavidin-binding epitopes are purified from cellular supernatant by streptavidin-beads. These results indicate that lentiviral particles were successfully tagged using these epitopes and captured from cellular supernatants.

Taking the results together, flankedccstreptag on a CD8 stalk was considered to perform better than flanked-ccstreptag on a GPI anchor (x2), as the former exhibited a higher binding efficiency in both cell sorting (FIG. 4) and viral purifying using streptavidin beads (FIG. 6).

Example 4—Analysis of Further Synthetic Epitope Tags

Further synthetic tags were assessed for the ability to facilitate the purification of lentiviral particles. The additional tags assessed were glutathione s transferase (GST), RTXep-QBEND10ep-RTXep-L8 (named RQR8) and poly-histidine-tag (his-tag). Complete annotated amino acid sequences of all three tags are shown in FIG. 7.

The efficiencies of the different tags (GST, RQR8 and His-tag) at purifying lentiviral particles from cellular media, was tested using the approach previously described for flankcedccstreptag (see Example 2), i.e. by sorting K562 cells expressing these tags on their surface. K562 cells were retrovirally transduced with flankedccstreptag, GST, RQR8 and H6 epitopes separately (FIG. 8, Pre-sorted column). Transduced cells represented a minority of the total population based on eGFP expression; therefore cells were not mixed with NT-K562 cells. Populations expressing flankedccstreptag at 10.5%, RQR8 at 9.75%, GST at 22.7% and H6 59.6% were thereafter sorted with Streptavidin Dynabeads, human rituximab previously incubated with protein-A bead, Glutathione magnetic beads and His-tag Dynabeads respectively.

Collected fractions were assessed for positive cells 12 days-post sorting. K562 cells expressing both flankedccstreptag and RQR8 were successfully sorted using their respective beads as indicated by the absence of eGFP positive cells in the flow fractions and their presence in the sorted fraction with 93.6% and 89.4% eGFP positive cells, respectively. Moreover, K562 cells expressing GST epitope were successfully purified from pre-sorting population with 91% eGFP positive cells present in the sorted fraction. However 10.6% eGFP positive cells were present in the flow through fraction which suggests that the beads were saturated with their ligand. Conversely, K562 expressing H6 sorting was less successful as only 26.1% of cells in the sorted fraction were eGFP positive while 71.1% of cells were eGFP negative. Additionally, 59.2% eGFP positive cells were in the flow-through. The GST and RQR8 tags therefore show the best activity with regard to purifying viral particles from cellular supernatant in the same manner as flankedccstreptag epitope.

To further demonstrate that GST and RQR8 epitopes are able to purify viral particles, 293T cells were retrovirally transduced with these tags to ensure almost complete expression of each cell population (FIG. 9) before proceeding with viral production.

In the same manner as above, epitopes-positive 293T cells were tripled transfected to produce VSV-G pseudotyped lentiviral particles using a second generation packaging system. After having treated the supernatant to remove cellular debris and suspension 293T cells, each supernatant was incubated with its respective ligand bound to magnetic beads and processed as stated in FIG. 10. Subsequently, freshly re-suspended beads/viral mixtures were used to transduce target NT-293T cells. Transduced cells were stained for transgene expression 120 hrs post-transduction in order to dilute out the beads (FIG. 10).

All supernatant produced from the 293T cells expressing flankedccstreptag (FIG. 10A), RQR8 (FIG. 10B) and GST (FIG. 10C) were producing functional viral particles as indicated by the high transduction efficiencies of the neat columns. Target cells transduced with the purified fraction of flankedccstreptag-tagged and RQR8-tagged-LVs resulted in 77.2% and 73.6% transduced cells, respectively.

These results together conclusively indicate that lentiviral particles can be purified from crude cellular supernatant using these synthetic tags and their respective ligand bound to a bead or a column. A schematic representation of this process is depicted in FIG. 11.

Example 5—Lentivirus Purification is Envelope Independent

The ability of the synthetic tags to purify a non-toxic viral envelope (e.g. RD114 variant RD-PRO) was determined using the flankedccstreptag and RQR8 tags.

RD-PRO pseudotyped viral particles were produced by triple transfection of 293T cells expressing the epitopes (FIG. 9) as mentioned above and sorted virus-beads mixture was used to transduce target 293T cells (FIG. 12).

Target cells transduced with neat LV in this experiment indicate that non-tagged-LV was capable of high transduction efficiency whereas flankedccstreptag- and RQR8-taggedLV neat had a lower transduction efficiency of 30.5% and 24.7%, respectively. These results indicate that using RDpro instead of VSV-G decreases the titre of viral particles produced. Nonetheless, target cells transduced with flankedccstreptag- and RQR8-tagged-LV sorted with their respective beads resulted in 28% and 14.1% transduced cells, respectively. Whereas non-tagged-LV incubated with streptavidin- and hRTX-protein-A-beads resulted in 0.42% and 1.10% positive cells for the transgene, indicating the beads specifically sort viral particles with their respective ligand on their surface. Moreover, for flankedccstreptag-tagged LV, incubation with beads resulted in the purification of almost all the viral particles compared to the flow through fraction of the non-tagged LV control. These results indicate that both flankedccstreptag and RQR8-tagged-LV purification is envelope independent.

Example 6—Transduction of Primary Peripheral Blood Mononuclear Cells

Primary peripheral bone mononuclear cells (PBMCs) were then transduced with RDpro-pseudotyped tag-purified LV. PBMCs were extracted from 2 healthy donors and transduced with both flankedccstreptag- and RQR8-tagged LV purified with their respective beads without the use of retronectin (FIG. 13).

The transduction efficiencies of all Neat conditions in both donors for control non-tagged-LV, RQR8-tagged LV (FIG. 13 A) and Flankedccstreptag-tagged LV (FIG. 13.B) were around 75%-90% positive for the encoded transgene. PBMCs of were successfully transduced with both RQR8- and Flankedccstreptag-tagged LV purified with their respective beads with 30-50% of positive cells for both tags in both donors (n=3, plotted on the graph in the bottom right corners). However their transduction efficiencies were lower than that of the Neat conditions. These results indicate that both RQR8- and Flankedccstreptag-tagged-RDpro-pseudotyped LV particles can be purified form cellular supernatant to successfully transduce primary PBMCs cells.

Example 7—Isolation of Purified Lentiviral Particles from the Tag Ligand

Purified tagged viral particles are removed from their respective ligands and concentrated.

Biotin is added to purified viral particles tagged with Flankedccstreptag such that the biotin competes for streptavidin binding and allows the flankedccstreptag displacement and subsequent elution of viral particles. For epitopes such as RQR8 that cannot be readily displaced by the addition of an active competitive binder to protein-A, a thrombin cleavage site (Leu-Val-Pro-Arg-Gly-Ser) is engineered on the linker of the epitopes. The addition of thrombin enables the protease to cleave between the Arg and the Gly residues allowing the effective removal of the viral particles from the immobilized epitopes bound to their ligands.

Example 8—Construction of Engineered Tagging Proteins Based on Lentiviral Envelope Proteins RD114 envelope is processed by removal of the signal peptide and by cleavage at a Furin cleavage site into SU and TM fragments (FIG. 14).

To generate RD114 SU tagged at its amino terminus with RQR, the RQR8 sequence was inserted just after the RD114 envelope signal peptide. To allow correct orientation for binding and to isolate from the envelope glycoprotein, a serine-glycine linker was inserted between RQR and SU. After processing, the RQR tag is at the extreme amino-terminus of the SU fragment.

To generate RD114 envelope TM tagged at its amino terminus with RQR, the tag was inserted just after the furin cleavage site. Again, a flexible linker was inserted between RQR and the TM fragment of RD114 envelope. After processing, RQR is accessible at the extreme amino-terminus of the TM domain.

To generate RD114 SU tagged at its amino terminus with flanked CC streptag, the tag sequence was inserted just after the RD114 envelope signal peptide. To allow correct orientation for binding and to isolate from the envelope glycoprotein, a serine-glycine linker was inserted between the tag and SU. After processing, the ccstreptag tag is at the extreme amino-terminus of the SU fragment.

To generate RD114 envelope TM tagged at its amino terminus with ccstreptag, the tag was inserted just after the furin cleavage site. Again, a flexible linker was inserted between the tag and the TM fragment of RD114 envelope. After processing, ccstreptag is accessible at the extreme amino-terminus of the TM domain.

Example 9—Analysis of Engineered Purification Tags

The ability of the engineered RD114 envelope proteins to encapsulate viral particles and result in infectious particles is determined. This is achieved by comparing titre of lentiviral vector generated with the tagged RD114 envelope with wild-type RD114 envelope.

Next, the ability to access the tags is tested. Cell lines are engineered to express the mutant RD114 and the cells are sorted using Rituximab/Protein A beads and Streptavidin beads respectively. Finally, the ability to capture lentiviral vector is determined by generating lentiviral vectors with these envelope proteins, capturing on a cognate solid phase and measuring the subsequent titre. These result are compared with stand-alone tagged proteins and in combination with stand-alone tagged proteins.

Example 10—Elution of Tagged Viral Particles with Biotin

Once flankedccstreptag-LV particles were purified using Streptavidin Dynabeads (0.5 mg/mL of LV supernatant), LV-bound beads were magnetically separated from cellular supernatant and washed 5 times with PBS using a magnetic rack. LV-bound beads were then resuspended in the elution solution that consists of plain DMEM containing 30 mM D-Biotin. Adding lyophilized powder of D-Biotin to plain DMEM followed by incubation at 37° C., with occasional vortex until powder had dissolved, made the later solution. LV-bound beads were incubated with elution solution for 2 hrs at 4° C. with rotation. Subsequently, tubes were placed on a magnetic rack to separate the unbound beads form the eluted purified viral particles.

The beads eluate and the flow-through eluate were analysed by flow cytometry and the results are shown in FIGS. 17 and 18. Flankedccstreptag-LV particles were shown to be eluted from streptavidin beads by Biotin-containing elution solution.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology, cellular immunology or related fields are intended to be within the scope of the following claims.

The invention claimed is:

1. A producer cell which expresses a tagging protein at the cell surface, such that retroviral vectors that bud from the producer cell are tagged with the tagging protein, wherein the tagging protein comprises:
   i) a binding domain that comprises amino acids 2-15 of SEQ ID NO: 2 and binds to streptavidin,
   ii) a membrane targeting domain that comprises a transmembrane domain and an endodomain; and
   iii) a spacer connecting the binding domain to the membrane targeting domain, wherein the spacer comprises a CD8 stalk or an equivalent thereof, wherein the tagging protein has binding affinity for streptavidin that facilitates purification of the tagged retroviral vectors from cellular supernatant with a capture moiety comprising streptavidin; and wherein the binding domain binds streptavidin with a lower affinity than biotin, so that biotin may be used to elute retroviral vectors produced by the cell and captured with the capture moiety.

2. The producer cell according to claim 1, wherein the spacer comprises a CD8 stalk or an equivalent thereof.

3. The producer cell according to claim 1, wherein the tagging protein also comprises a cleavage site, cleavage at which releases retroviral vectors bound to a capture moiety that comprises streptavidin.

4. The producer cell according to claim 3, wherein the tagging protein comprises a linker between the binding domain and the spacer, which linker is or comprises the cleavage site.

5. The producer cell according to claim 3, wherein the cleavage site is a thrombin cleavage site.

6. The producer cell according to claim 1, wherein the transmembrane domain and endodomain are the same as the transmembrane and endodomain of a retroviral vector envelope protein.

7. The producer cell according to claim 6, which comprises the transmembrane domain and endodomain from RD-PRO envelope protein as set out in amino acids 509-565 of SEQ ID NO: 39.

8. A retroviral vector which comprises a producer cell-derived tagging protein, said tagging protein comprising:
   i) a binding domain that comprises amino acids 2-15 of SEQ ID NO: 2 and binds to streptavidin, ii) a membrane targeting domain that comprises a transmembrane domain and an endodomain; and iii) a spacer connecting the binding domain to the membrane targeting domain, wherein the spacer comprises a CD8 stalk or an equivalent thereof, and wherein the binding domain binds streptavidin with a lower affinity than biotin, so that biotin may be used to elute the retroviral vector following capture with a capture moiety comprising streptavidin.

9. The producer cell according to claim 1 which comprises genes encoding retroviral Gag, Pol and Env proteins stably integrated within the cell genome.

10. A producer cell which expresses a tagging protein at the cell surface, such that retroviral vectors produced by the cell are tagged with the tagging protein, wherein the tagging protein comprises:

i) a binding domain that comprises two or more streptavidin-binding epitopes, comprising at least one linker between the streptavidin-binding epitopes, each of said streptavidin-binding epitopes comprising amino acids 2-15 of SEQ ID NO: 2, and that binds streptavidin; and ii) a membrane targeting domain comprising a glycosyl-phosphatidylinositol (GPI) anchor;

wherein the tagging protein has binding affinity for streptavidin that facilitates purification of the tagged retroviral vectors from cellular supernatant with a capture moiety comprising streptavidin; and wherein the binding domain binds streptavidin with a lower affinity than biotin, so that biotin may be used to elute retroviral vectors produced by the cell and captured with the capture moiety.

11. The producer cell according to claim 10, wherein the tagging protein further comprises a linker between the binding domain and the GPI anchor, which linker is or comprises a cleavage site.

12. The producer cell according to claim 10, wherein the tagging protein further comprises a linker between the binding domain and the GPI anchor, which linker is or comprises a cleavage site.

13. A producer cell according to claim 10, wherein the binding domain comprises the amino acid sequence shown as SEQ ID NO: 5.

14. The producer cell according to claim 10, which comprises genes encoding retroviral Gag, Pol and Env proteins stably integrated within the cell genome.

15. A retroviral vector which comprises a producer cell-derived tagging protein, said tagging protein comprising:

i) a binding domain that comprises two or more streptavidin-binding epitopes, each of said streptavidin-binding epitopes comprising amino acids 2-15 of SEQ ID NO: 2, and further comprises at least one linker between the streptavidin-binding epitopes, wherein the binding domain binds streptavidin; and ii) a membrane targeting domain comprising a glycosyl-phosphatidylinositol (GPI) anchor;

wherein the tagging protein has binding affinity for streptavidin that facilitates purification of the tagged retroviral vectors from cellular supernatant with a capture moiety comprising streptavidin; and wherein the binding domain binds streptavidin with a lower affinity than biotin, so that biotin may be used to elute retroviral vectors captured with a capture moiety comprising streptavidin.

16. The producer cell according to claim 8, wherein the spacer comprises a CD8 stalk.

17. The retroviral vector according to claim 10, wherein the tagging protein further comprises a linker between the binding domain and the GPI anchor, which linker is or comprises a cleavage site.

18. A method for making a producer cell according to claim 1, which comprises the step of introducing a nucleic acid which encodes the tagging protein into a cell, such that the tagging protein is expressed at the cell surface.

19. A method for purifying a retroviral vector according to claim 8 which comprises a step of capturing the retroviral vector using a capture moiety that comprises streptavidin.

20. The method according to claim 19, which also comprises a step of eluting the retroviral vector from the capture moiety with biotin.

* * * * *